(12) United States Patent
Banzai et al.

(10) Patent No.: US 8,071,332 B2
(45) Date of Patent: Dec. 6, 2011

(54) RECOMBINANT MAMMAL CELLS, METHOD OF PRODUCING THEREOF, AND METHOD OF PRODUCING PROTEINS OF INTEREST

(75) Inventors: Toshiaki Banzai, Fukuoka-ken (JP);
Yukiko Koyama, Fukuoka-ken (JP);
Shuji Sonezaki, Fukuoka-ken (JP)

(73) Assignee: Toto Ltd., Fukuoka-ken (JP)

( * ) Notice: Subject to any disclaimer, the term of this patent is extended or adjusted under 35 U.S.C. 154(b) by 418 days.

(21) Appl. No.: 12/222,412

(22) Filed: Aug. 8, 2008

(65) Prior Publication Data
US 2009/0117615 A1 May 7, 2009

Related U.S. Application Data

(60) Provisional application No. 60/955,738, filed on Aug. 14, 2007.

(30) Foreign Application Priority Data

Aug. 10, 2007 (JP) ................................ 2007-210122
Jul. 24, 2008 (JP) ................................ 2008-191278

(51) Int. Cl.
*C12P 21/06* (2006.01)
*C12N 5/00* (2006.01)

(52) U.S. Cl. ...................................... 435/69.1; 435/325

(58) Field of Classification Search .................. 435/69.1, 435/325
See application file for complete search history.

(56) References Cited

U.S. PATENT DOCUMENTS

| 6,846,676 B2 | 1/2005 | Selden et al. |
| 2003/0203447 A1 | 10/2003 | Horwitz |
| 2007/0281334 A1 | 12/2007 | Horwitz |

FOREIGN PATENT DOCUMENTS

| JP | 7-500969 | 2/1995 |
| JP | 2005-528925 | 9/2005 |

OTHER PUBLICATIONS

Y. Koyama et al., "Stable Expression of a Heterogeneous gene Introduced via Gene Targeting into the HPRT Locus of Human Fibrosarcoma Cells", Biotechnology and Bioengineering, vol. 95, No. 6, pp. 1052-1060, Dec. 20, 2006.
R. Hirata et al., "Targeted transgene insertion into human chromosomes by adeno-associated virus vectors", Nature Biotechnology, vol. 20, pp. 735-738, Jul. 2002.
P. C. Hendrie et al., "Chromosomal Integration and Homologous Gene Targeting by Replication-Incompetent Vectors Based on the Autonomous Parvovirus Minute Virus and Mice", Journal of Virology, vol. 77, No. 24, pp. 13136-13145, Dec. 2003.
J. D. Heaney et al., "Tissue-specific expression of a BAC transgene targeted to the *Hprt* locus in mouse embryonic stem cells", Genomics, vol. 83, pp. 1072-1082, 2004.
D. Clavatta et al., "A DNA insulator prevents repression of a targeted X-linked transgene but not its random or X inactivation", Proc. Natl. Acad. Sci., vol. 103, No. 26, pp. 9958-9963, Jun. 27, 2006.
B. K. Jones et al., "The Human Growth Hormone Gene is Regulated by a Multicomponent Locus Control Region", Molecular and Cellular Biology, vol. 15, No. 12, pp. 7010-7021, Dec. 1995.
English translation of the International Preliminary Report on Patentability.
Japanese Office Action issued on Mar. 10, 2009 in corresponding JP Appln. No. 2008-555549 in Japanese language.
Newsletter of Japan Society for Comparative Endocrinology, 2006, vol. 2006, No. 122, pp. 23-31 (cited reference) with partial English translation thereof.

*Primary Examiner* — Karen Carlson
(74) *Attorney, Agent, or Firm* — Wenderoth, Lind & Ponack, L.L.P.

(57) ABSTRACT

The present invention relates to a method of expressing an objective protein at a high level and stably as well as for a long period even in the absence of a selection drug with a recombinant mammal cell. More particularly, the present invention relates to a method of producing an objective protein by providing a recombinant mammal cell having multiple copies of the exogenous objective protein gene expression unit integrated into a hypoxanthine-phosphoribosyl transferase enzyme (hprt) gene locus and culturing said cell.

19 Claims, 13 Drawing Sheets

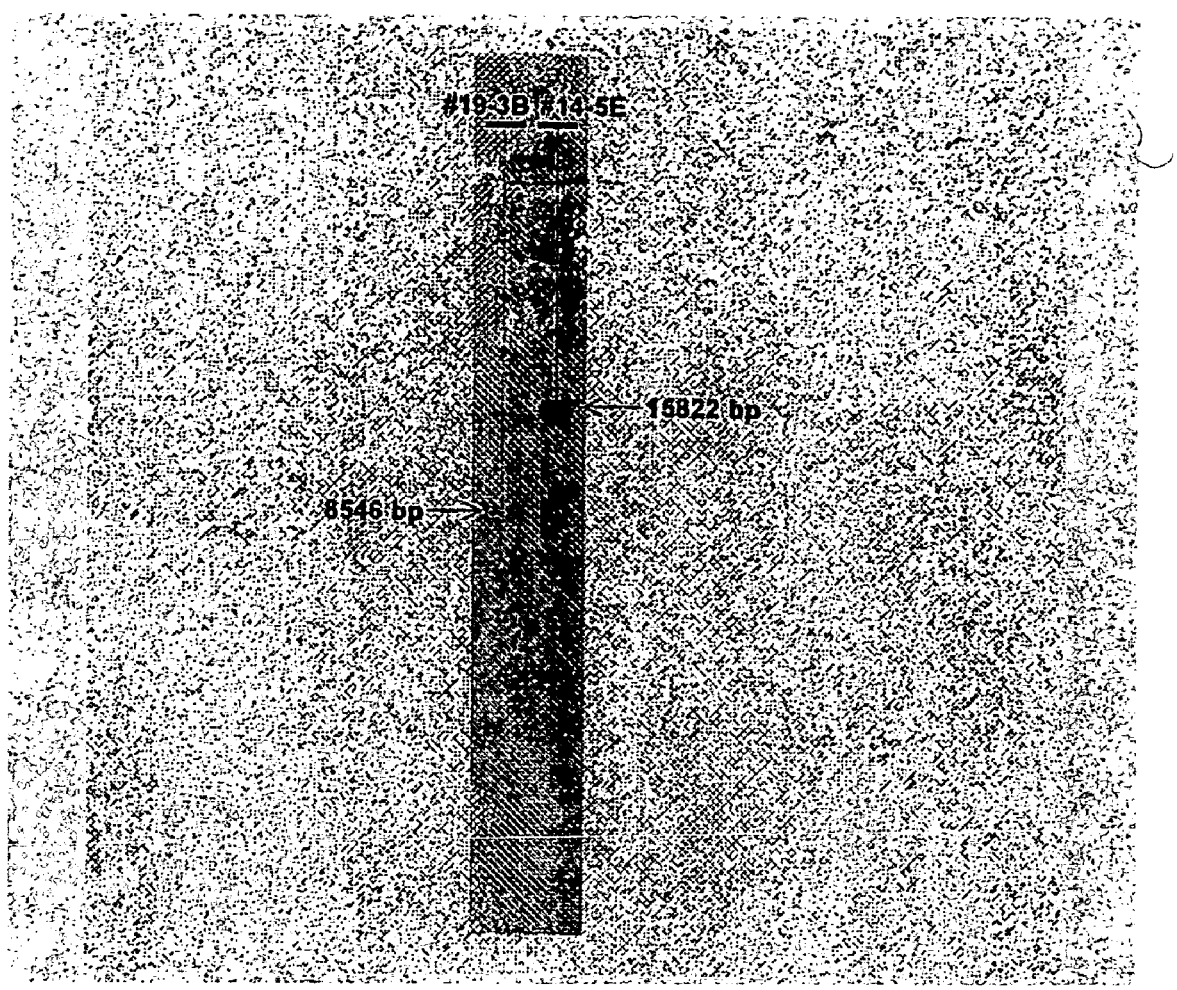
F I G. 2

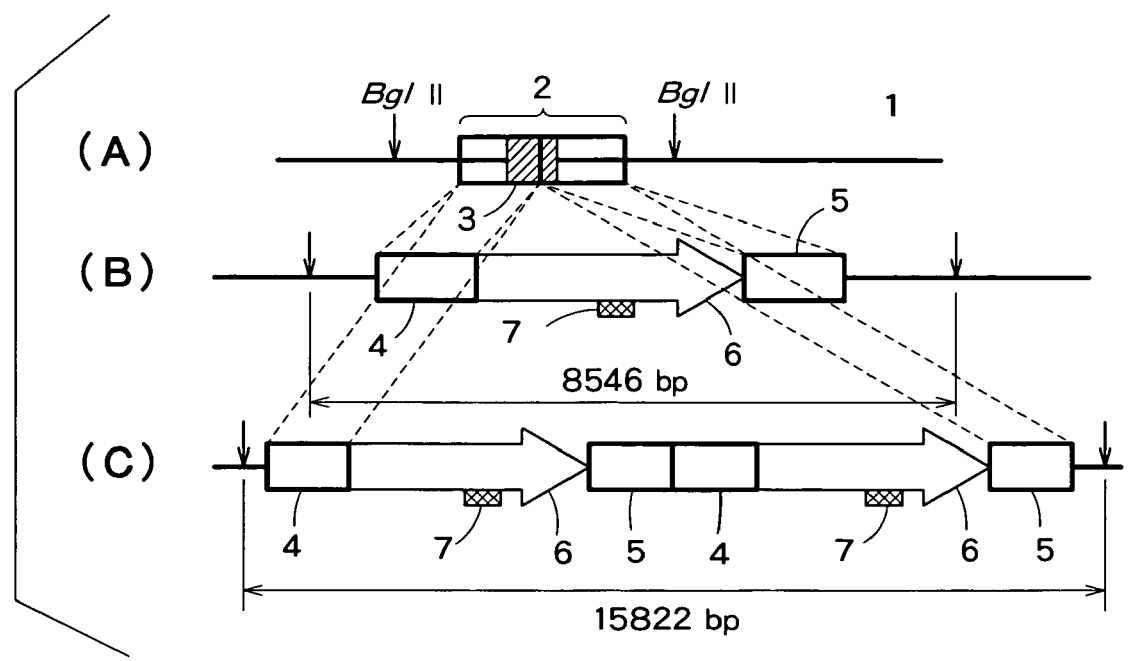
F I G. 3

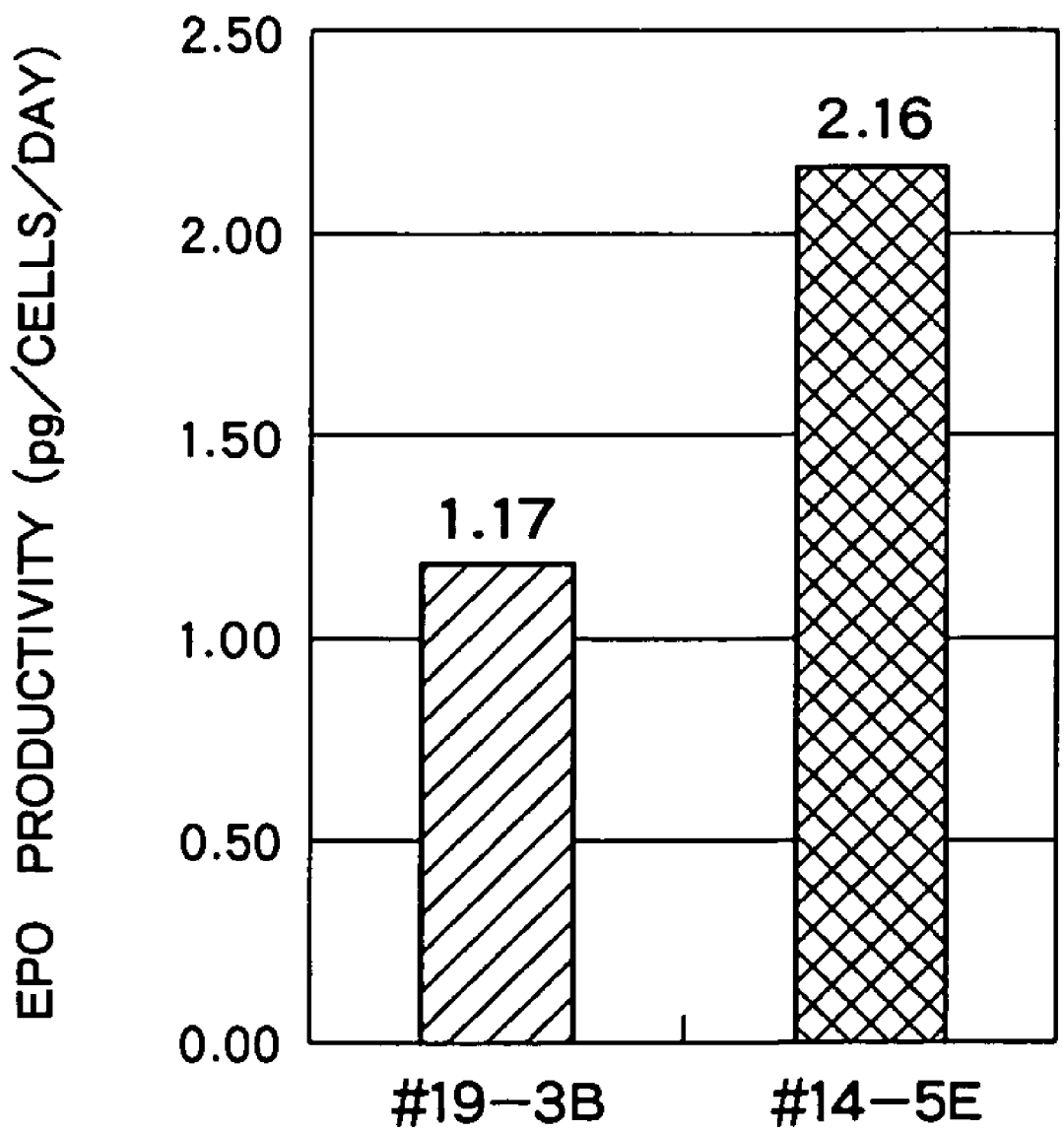
F I G. 4

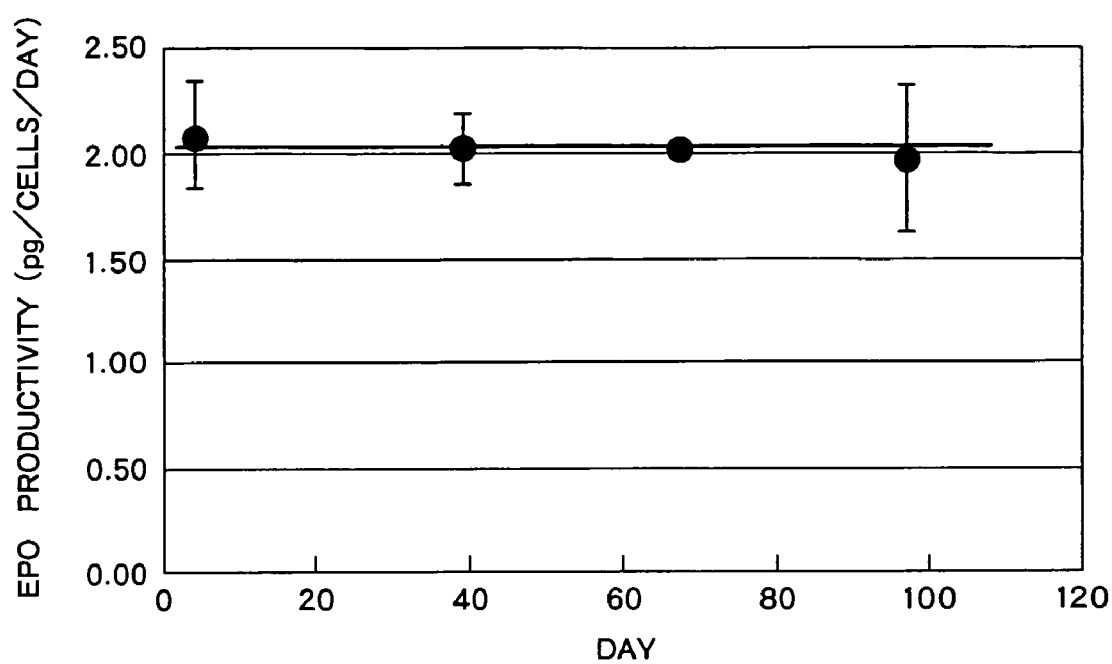
F I G. 5

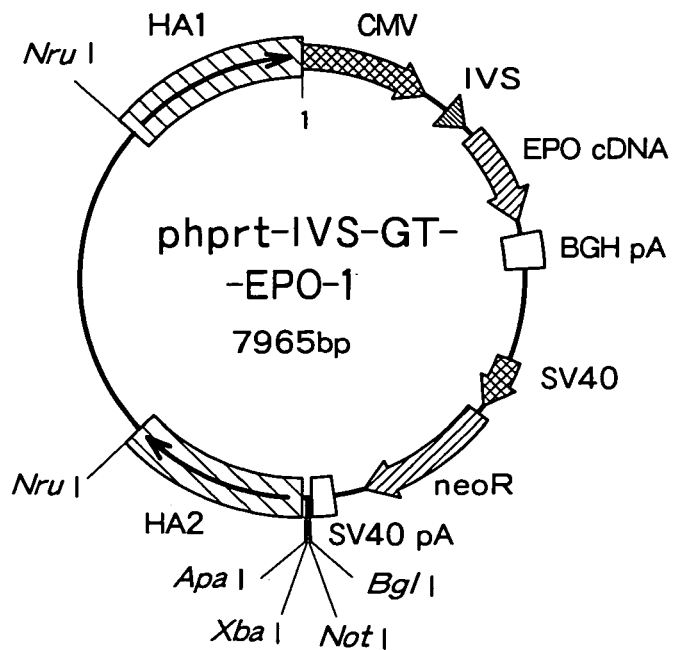
F I G. 7
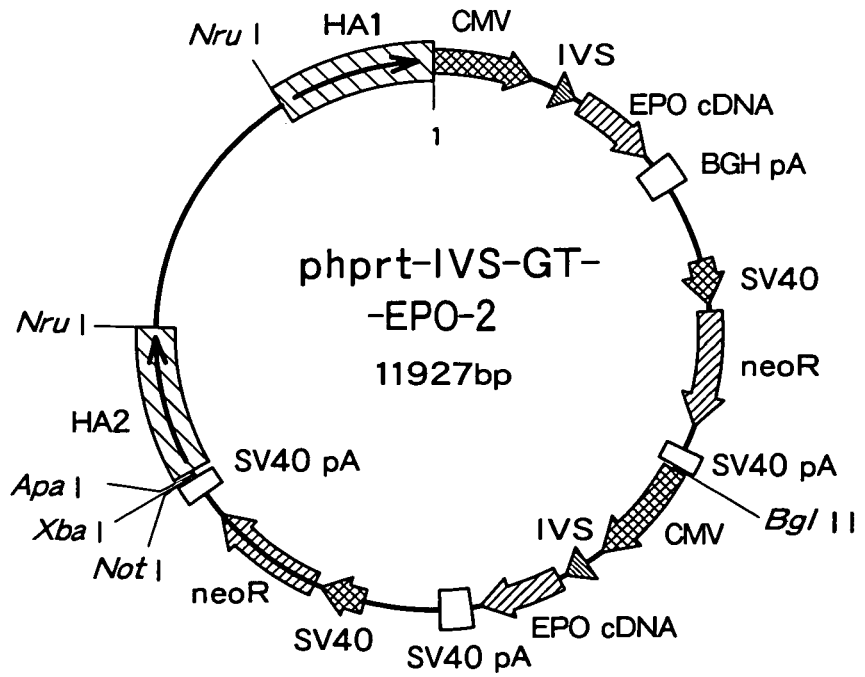
F I G. 8

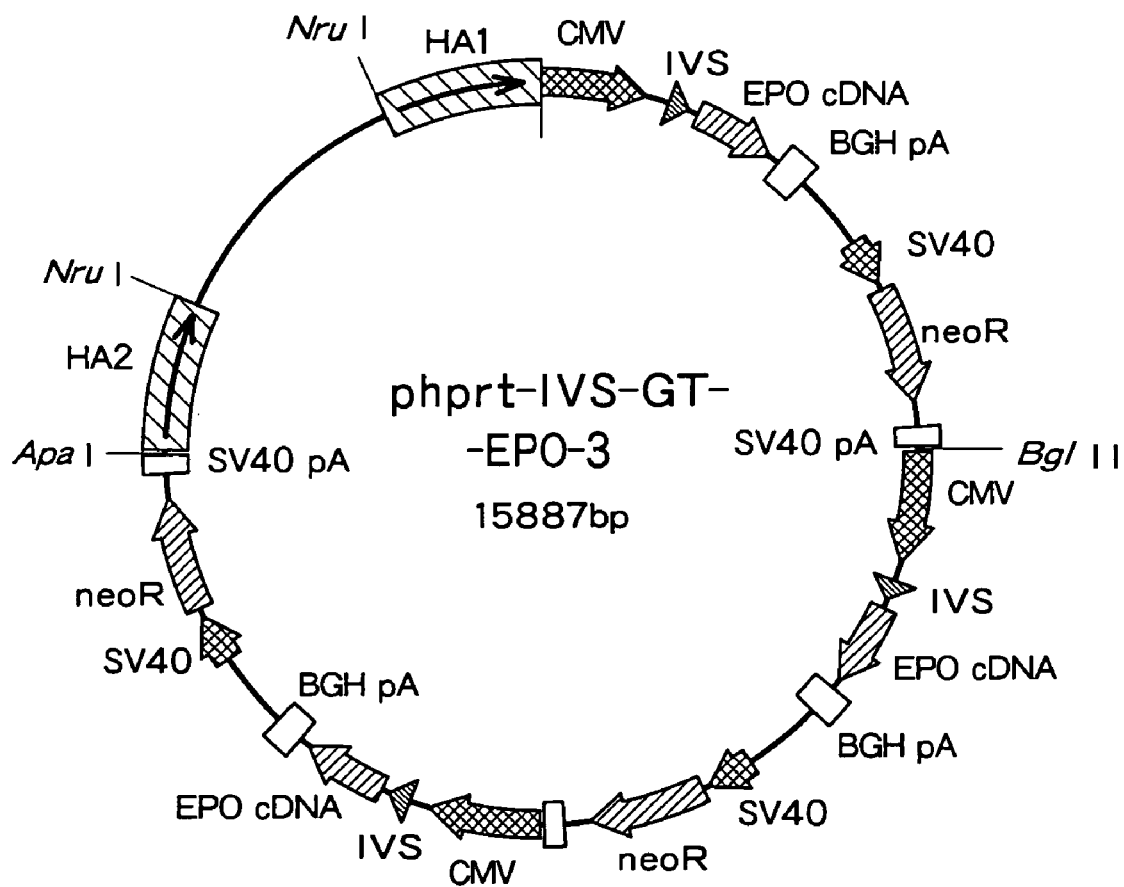
F I G. 9

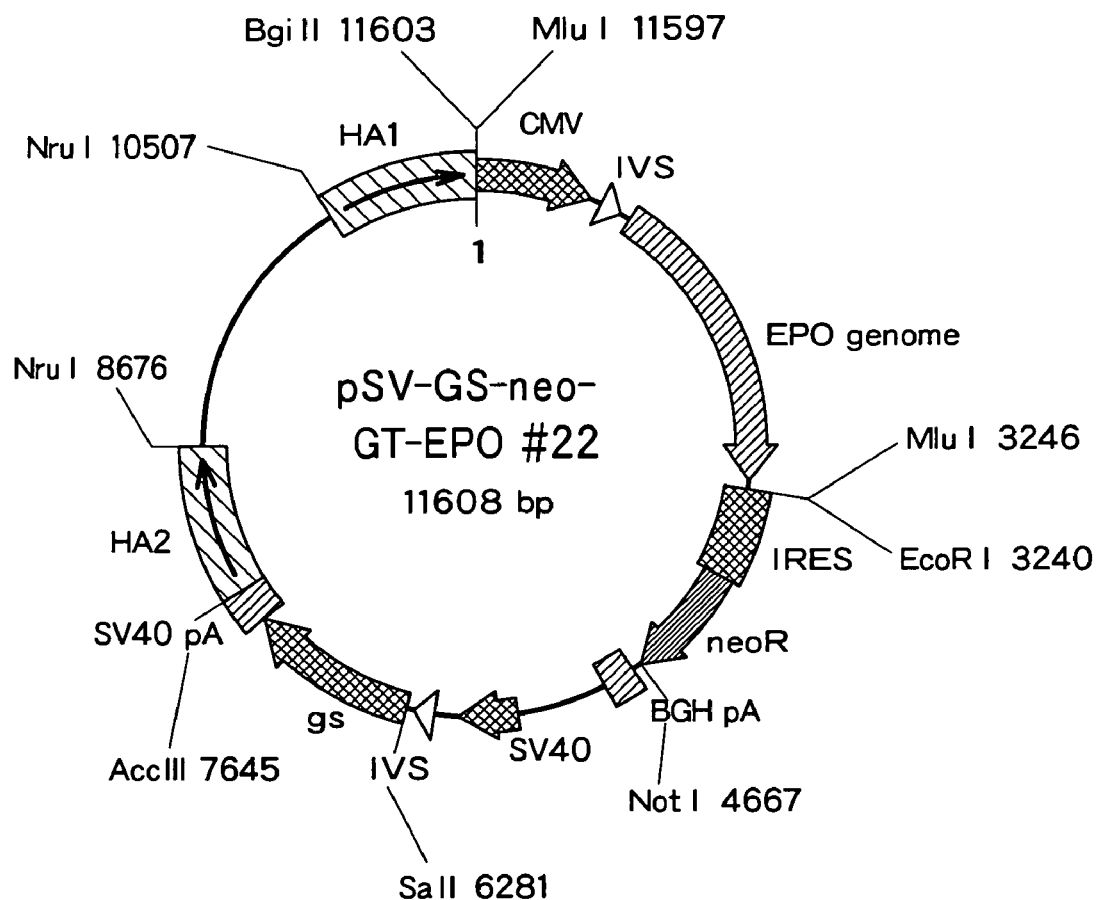
F I G. 11

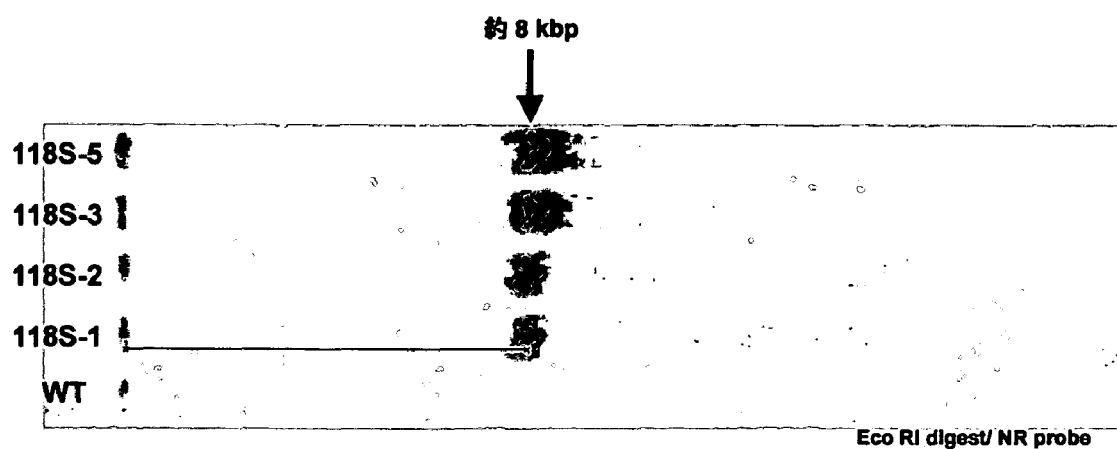
F I G. 13

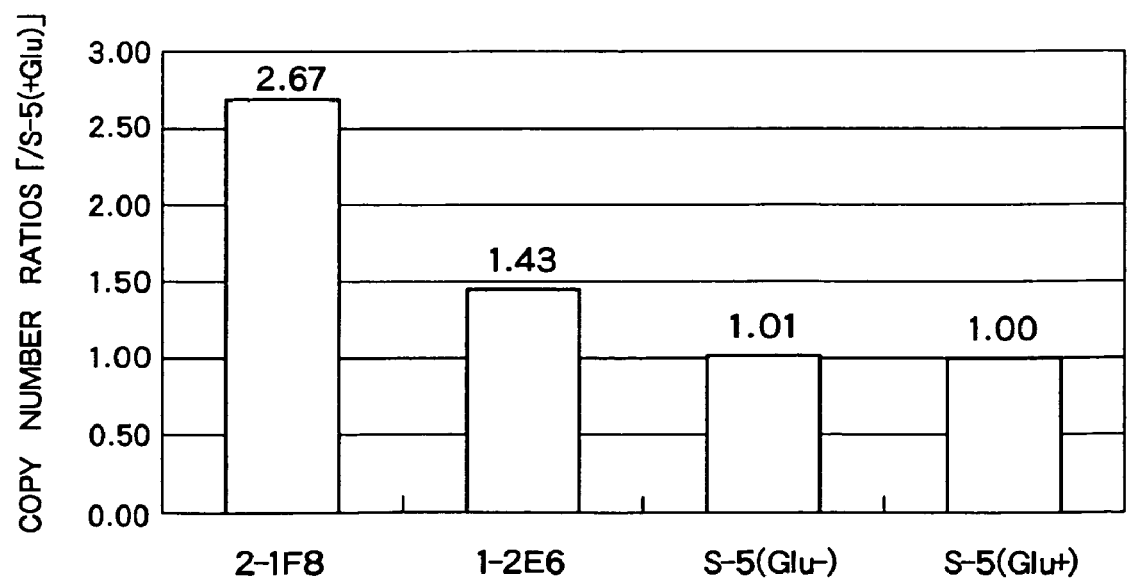
F I G. 14

SEQUENCE LISTING

```
<160> NUMBER OF SEQ ID NOS: 33

<210> SEQ ID NO 1
<211> LENGTH: 40
<212> TYPE: DNA
<213> ORGANISM: Artificial
<220> FEATURE:
<223> OTHER INFORMATION: primer

<400> SEQUENCE: 1
cctgcaggtc gcgattggta cttgttcagc tttattcaag                    40

<210> SEQ ID NO 2
<211> LENGTH: 41
<212> TYPE: DNA
<213> ORGANISM: Artificial
<220> FEATURE:
<223> OTHER INFORMATION: primer

<400> SEQUENCE: 2
gtcgacaagg acgcgttctg ataaaatcta cagtcatagg a                  41

<210> SEQ ID NO 3
<211> LENGTH: 67
<212> TYPE: DNA
<213> ORGANISM: Artificial
<220> FEATURE:
<223> OTHER INFORMATION: primer

<400> SEQUENCE: 3
gtcgacctct agctagagct tggcgtaatc atggtctccg gagactgaag agctattgtg   60
tgagtat                                                            67

<210> SEQ ID NO 4
<211> LENGTH: 46
```

```
<212> TYPE: DNA
<213> ORGANISM: Artificial
<220> FEATURE:
<223> OTHER INFORMATION: primer

<400> SEQUENCE: 4
acatgttctc ttaagtcgcg aagtagtgtt atgatgtatg ggcata                    46

<210> SEQ ID NO 5
<211> LENGTH: 35
<212> TYPE: DNA
<213> ORGANISM: Artificial
<220> FEATURE:
<223> OTHER INFORMATION: primer

<400> SEQUENCE: 5
acatgtgagc aaaaggccag caaaaggcca ggaac                                35

<210> SEQ ID NO 6
<211> LENGTH: 40
<212> TYPE: DNA
<213> ORGANISM: Artificial
<220> FEATURE:
<223> OTHER INFORMATION: primer

<400> SEQUENCE: 6
cctgcaggga cgtcaggtgg cactttttcgg ggaaatgtgc                           40

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
ccttgctagc atgggggtgc acggtgagta                                      30

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
ccttgaattc tcatctgtcc cctgtcctgc                                      30

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
ccttacgcgt tcaatattgg ccattagcca                                      30

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
ccttgctagc ctatagtgag tcgtattaag                                      30
```

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
ccttgctagc atggggtgc acgaatgtcc                                     30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
ctacgcgtag atctgacgtc aggtggcact                                    30

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
ctgtcgacgc ggccgcacat gtgagcaaaa                                    30

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
ctacgcgttc tagagacgtc aggtggcact                                    30

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
ctgtcgacgg gcccacatgt gagcaaaagg                                    30

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
aaagttctct cctttcagcc ttctgtacac                                    30

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
gcaccttcca gggtcaagga                                         20

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
acaagttaaa aggagcttat gggtaggaag                              30

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ccttctatcg ccttcttgac                                         20

<210> SEQ ID NO 20
<211> LENGTH: 29
<212> TYPE: DNA
<213> ORGANISM: Artificial
<220> FEATURE:
<223> OTHER INFORMATION: primer

<400> SEQUENCE: 20
ccttcccggg atgattgaac aagatggat                               29

<210> SEQ ID NO 21
<211> LENGTH: 28
<212> TYPE: DNA
<213> ORGANISM: Artificial
<220> FEATURE:
<223> OTHER INFORMATION: primer

<400> SEQUENCE: 21
ccttgcggcc gctcagaaga actcgtca                                28

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
gtcgacgata tctctagatg tgccttctag                              30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
ccttggatcc tccggaagcc atagagccca                              30

<210> SEQ ID NO 24
<211> LENGTH: 41

<212> TYPE: DNA
<213> ORGANISM: Artificial
<220> FEATURE:
<223> OTHER INFORMATION: primer

<400> SEQUENCE: 24
ccttaggcct aggcttttgc aaaaagcttt attgcggtag t        41

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25
tctagagata tcgtcgacct atagtgagtc                     30

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
ccttgtcgac caccatgacc acctcagcaa                     30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
cctttctaga ttaattttg tactggaagg                      30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
ccttgctagc atggggtgc acggtgagta                      30

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29
ccttgaattc tcatctgtcc cctgtcctgc                     30

<210> SEQ ID NO 30
<211> LENGTH: 47
<212> TYPE: DNA
<213> ORGANISM: Artificial
<220> FEATURE:
<223> OTHER INFORMATION: primer

<400> SEQUENCE: 30
gtcgacaagg agatctacgc gttctgataa aatctacagt catagga  47

```
<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
accccttttc ggtgacagaa                                              20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
tcgccggttt cattgagaag                                              20

<210> SEQ ID NO 33
<211> LENGTH: 16
<212> TYPE: DNA
<213> ORGANISM: Artificial
<220> FEATURE:
<223> OTHER INFORMATION: probe

<400> SEQUENCE: 33
ccctcatccg cacgtg                                                  16
```

RECOMBINANT MAMMAL CELLS, METHOD OF PRODUCING THEREOF, AND METHOD OF PRODUCING PROTEINS OF INTEREST

REFERENCE TO RELATED APPLICATIONS

The present patent application claims priorities to Japanese Patent Application No. 2007-210122 filed on Aug. 10, 2007, U.S. Provisional Patent Application No. 60/955,738 filed on Aug. 14, 2007, and Japanese Patent Application No. 2008-191278 filed on Jul. 24, 2008, the entire disclosure of which are incorporated herein by reference.

BACKGROUND OF THE INVENTION

1. Field of the Invention

The present invention relates to a recombinant mammal cell and a method of producing a protein with use of the cell.

2. Background Art

There are known a variety of recombinant protein producing systems with procaryotes or eucaryotes as a host cell. According to the recombinant protein producing system with a mammal cell as the host cell, it is possible to subject proteins derived from higher animals including human to post-translational modifications such as the addition of polysaccharide chain, folding and phosphorylation in a similar manner to those produced in vivo.

The post-translational modification is necessary for reproducing physiological activities of a native protein in the recombinant protein. Thus, a protein producing system with a mammal cell as the host cell is preferably used in recombinant protein producing systems used in medicaments for which such physiological activities are particularly needed.

In the industrial production of pharmaceutical proteins, it is important to stably maintain the expression of a protein in a high level. Particularly, the maintenance of the stable expression level is important not only to the respect of cost but also to the verification of the identity and safety as pharmaceutical proteins. In order to use the recombinant protein producing cell for its production in industrial scales, it is necessary to magnify a scale for culturing the clone of the recombinant protein producing cell. It is usually estimated for magnifying the scale that the clone just developed must be subjected to at least 60 cell divisions (Brown, M. E. et al. (1992) Cytotechnology, 9, 231-236.), and the expression level must be maintained constant during the cell division.

The specific productivity of the recombinant clonal cell may also be reduced to such a level that is hardly used as production cells during or after period for magnifying the culture scale, and in this case the development period over several months will come to nothing (Barnes, L. M. et al. (2003) Biotechnol. Bioeng. 81, 631-639).

The use of selection drugs during the periods of scale-up and practical production rises the costs not only of culture but also of purification processes in order to avoid the risk of polluting pharmaceuticals with toxic agents. Thus, the production of the recombinant clonal cell is generally carried out without addition of selection drugs.

The recombinant mammal clonal cell which produces the objective protein is required to have the specific productivity at high level as well as the property which enables to stably maintain the specific productivity level without addition of the selection drug.

Specific productivity in high levels is generally achieved by a process for increasing the copy number of an exogenous gene which codes for an objective protein by gene amplification technology, and systems such as CHO-DHFR and GS-NS0 have been established as practical techniques (Japanese Patent Publication No. 7-40933; Werner R. G. et al. (1998) Arzneim.-Forsch./Drug Res 48, 870-880, and the like).

However, it has been confirmed that when clonal cells having increased levels of specific productivity are selected and then the selected clonal cells are continuously cultured in a medium containing no selection drugs, the level of specific productivity is lowered or vanished in most of the clones. Furthermore, it has also been described in literatures that the expression level of an objective protein is not always increased in proportion to the increased copy number of an integrated gene (Japanese Patent Application Laid-Open Disclosure No. 2002-541854; Kim, N. S. et al. (1998) Biotechnol. Bioeng., 60, 679-688; and the like).

It has been reported that the decreased level of specific productivity or the disappeared production of the objective protein are primarily caused by the decreased copy number of genes (Kim, N. S. et al. (1998) Biotechnol. Bioeng., 60, 679-688, Kim, S. J. (1998) Biotechnol. Bioeng. 58, 73-84, Yoshikawa, T. et al. (2000) Biotechnol. Progr. 16, 710-715; and the like).

It has been described in the literatures as Repeat-Induced Gene Silencing (RIGS) that such decrease or disappearance of the specific productivity levels are also caused by repeated integrations of multiple gene copies of identical sequence in tandem (Henikoff, S. (1998) Bioessays 20, 532-535; Garrick, D. et al. (1998) Nat. Genet. 18, 56-59). It has been reported that RIGS may be caused also in 2-3 copies of gene (McBurney, M. W. (2002) Exp. Cell Res. 274, 1-8).

Furthermore, no satisfactory solutions have hitherto been presented with respect to stability of the specific productivity level of an objective protein. Clonal selection is now empirically carried out on the basis of data which have been accumulated with regard to the growth rate and productivity during the culture of clone for a long period. According to this empirical process, it is rarely accomplished to get a clonal cell having a stable specific productivity level of the objective protein, which can probably be obtained by chance (Barnes, L. M. et al. (2003) Biotechnol. Bioeng. 81, 631-639).

The present inventors have previously reported a method for obtaining a recombinant cell in which an expression unit of the green fluorescent protein (GFP) as a single copy is integrated into the locus of the hypoxanthine-phosphoribosyl transferase (hprt) gene by homologous recombination (Biotechnol. Bioeng., 95(6): 1052-1060, 2006). The clonal cell stably maintains the specific productivity level even during its cultivation for a long period in the absence of the selection drug.

In the case of obtaining usual random recombinant clonal cells, multiple copies of exogenous genes are often integrated into the identical chromosomal site (Martin, D. I. K. and Whitelaw, E. (1996) Bioessays, 18, 919-923). These copies may be a target of RIGS. On the contrary, it is possible to avoid RIGS in the integration of one copy by homologous recombination (Whitelaw, E. et al. (2001) Methods in Mol. Biol. 158, 351-368).

On the other hand, it is known also in the integration of one copy that the stability of the specific productivity level largely varies depending on chromosomal sites for integration (Walters, M. C. et al. (2007) Genes Dev. 10, 185-195).

It can be found from these facts that the hprt genetic site having a copy of an exogenous gene integrated therein is excellent for maintaining the stability of the specific productivity level. On the other hand, it is however impossible to estimate the stability of the specific productivity level as well as the possibility of avoiding RIGS when multiple copies of an exogenous gene are integrated into the hprt genetic site.

In addition, Japanese Patent Application Laid-Open Disclosure No. H7-500969 discloses that an erythropoietin gene expression unit has been integrated into the hprt gene locus of HT1080 cell derived from human fibrosarcoma by homologous recombination. However, no expression of erythropoietin gene has been confirmed, nor integration of multiple copies has been found.

SUMMARY OF THE INVENTION

The present inventors have now found an unexpected information that mammal cell obtained by integrating multiple copies of the gene of an objective protein into the hprt gene locus is capable of stably maintaining the specific productivity level of the objective protein for a long period and the specific productivity level is proportional to the copy number of the objective protein gene integrated. The present invention is based on such findings.

Thus, the object of the present invention is to provide a recombinant cell in which an objective protein can be stably prepared at a high level and a method of producing it as well as a method of producing the objective protein with the recombinant cell.

In this connection, the mammal cell according to the present invention is the one in which multiple copies of the gene of the exogenous objective protein are integrated into the hprt gene locus.

Also, the method of producing the mammal cell according to the present invention comprises integrating multiple copies of the gene of the exogenous objective protein into the hprt gene locus.

In addition, the method of producing an objective protein according to the present invention comprises culturing the mammal cell to produce the objective protein.

BRIEF DESCRIPTION OF THE DRAWINGS

FIG. 2 is a photogram which illustrates the Southern blot hybridization in the recombinant clones (#14-5E, #19-3B).

FIG. 3(A) illustrates the targeting site of homologous recombination in the hprt gene; (B) illustrates a schematic view in which 1 copy of DNA sequence for introducing phprt-GT-EPO gene has been integrated into the genomic DNA of a clonic cell by homologous recombination; and (C) illustrates a schematic view in which 2 copies of DNA sequence for phprt-GT-EPO gene have been integrated into the genomic DNA of a clonic cell by homologous recombination.

FIG. 4 is a graph which shows the productivity of EPO in recombinant clones (#14-5E, #19-3B) cultured in a G418- and 6TG-free medium just after establishment.

FIG. 5 is a graph which shows the productivities of EPO in the recombinant clones (#14-5E) cultured in a G418- and 6TG-free medium for 96 days.

FIG. 7 illustrates a schematic view of a plasmid vector of a phprt-IVS-GT-EPO-1 containing an erythropoietin gene as a single copy.

FIG. 8 illustrates a schematic view of a plasmid vector of a phprt-IVS-GT-EPO-2 containing two copies of an erythropoietin gene.

FIG. 9 illustrates a schematic view of a plasmid vector of a phprt-IVS-GT-EPO-3 containing three copies of an erythropoietin gene.

FIG. 11 illustrates a schematic view of a plasmid vector of a pSV-GS-neo-GT-EPO #22 containing an erythropoietin gene and a gs gene amplification marker.

FIG. 13 is a photogram which illustrates Southern hybridization in the recombinant clones (118S-1, 118S-2, 118S-3, 118S-5).

FIG. 14 illustrates the analysis of the copy number of gs gene in a genome by real-time quantitative PCR. 2-1F8 and 1-2E6 are cells which exhibited resistance to 5 µM of MSX, and S-5 (Glu−) and S-5 (Glu+) are the 118S-5 cell which was maintained in a medium non-supplemented or supplemented with glutamine, respectively. The results are the relative values to S-5 (Glu+).

Figure 1:
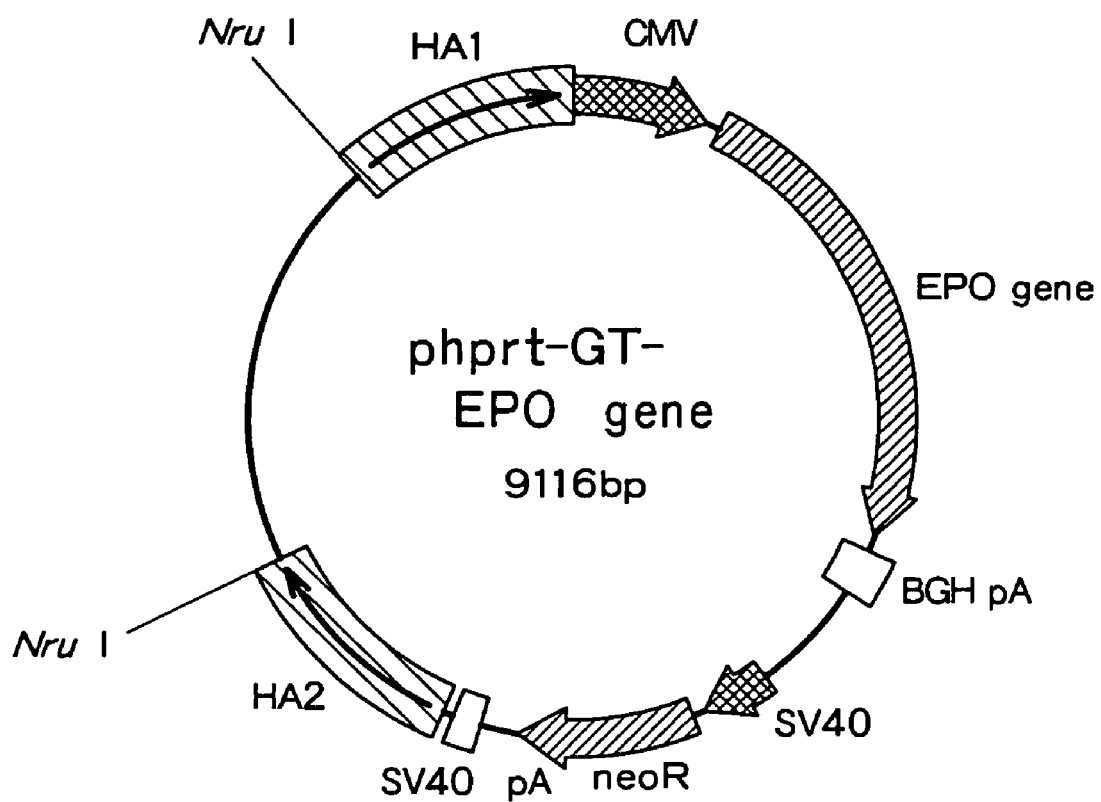
FIG. 1 illustrates a schematic view of a plasmid vector of a phprt-GT-EPO gene containing an erythropoietin gene as a single copy.

DETAILED DESCRIPTION OF THE INVENTION hprt Gene Locus/Integration of Multiple Copies of an Objective Protein Gene

In the method of producing an objective protein according to the present invention, the hprt gene locus is provided as a targeting region for the gene recombination of multiple copies of the objective protein. The hprt gene is known as one of housekeeping genes which are present in the long arm of human X chromosome. When multiple copies of exogenous objective protein gene integrated into the hprt gene locus are expressed, the specific productivity level of the objective protein is increased approximately in proportion to the copy number. Furthermore, it is possible to maintain stably the amount of the expression over a long period of time. According to the preferred embodiment of the present invention, it is possible to maintain the stability over a long period of time even in the absence of selection drug.

The term "multiple copies of an exogenous gene" herein means the presence of 2 or more substantially identical genes or gene expression units on the hprt gene locus. In this connection, multiple copies of the expression units may not always be trascripted to the same direction and may be present all in tandem repeatedly to the same direction. Other DNA sequences may be contained between genes or expression units repeatedly present. Also, the term "in proportion to" means that the specific productivity level is in the positive proportional relationship with the gene copies, and preferably means that the specific productivity level ascends additively depending on the increase of the gene copies.

While multiple copies of an objective protein gene have conventionally been integrated in anticipation of the increased amount of their expression, such increase is hardly proportional to the integrated copies in most of the cases. Thus, the effect of the increased amount of their expression in proportion to the integrated copies is extremely advantageous and extraordinary to the production of an objective protein.

In the production process according to the present invention, the copy number of an exogenous objective protein gene is in the range of 2 or more, preferably with the upper limit of about 500, more preferably with the upper limit of 100, further preferably with the upper limit of 10 and further preferably of 3. In addition, the multiple copies of the objective protein gene can be integrated into the hprt gene locus with for example vector described in the following.

Objective Protein Gene

The objective protein gene, whether it is a sequence derived from cDNA or a structural gene containing natural intron derived from genomic DNA, may be appropriately used. Also, the objective protein gene preferably codes for proteins useful as pharmaceuticals. The protein, whether it is accumulated within cell or excreted extracellularly, may be used in the present invention. Also, the objective protein includes enzyme, cytokine, hormone, antibody, coagulation factor, regulatory protein, receptor and the like, and more specifically erythropoietin, monoclonal antibody, tissue-specific plasminogen activator, granulocyte colony activator and the like.

Expression Unit

The objective protein gene described above is preferably integrated into the hprt gene locus as an expression unit containing elements required for the expression such as a promoter sequence or a transcription termination signal sequence. Thus, according to an embodiment of the present invention, the objective protein gene is integrated into the hprt gene locus as an expression unit containing at least a promoter sequence and a transcription termination signal sequence.

In addition, the elements required for the expression such as a promoter sequence or a transcription termination signal sequence in the expression unit may be appropriately determined depending on the kind or nature of the objective protein gene, and the suitable promoter sequence includes, for example, CMV promoter, SV40 promoter, and the like. Also, the transcription termination signal sequence includes, for example, BGH poly-A signal sequence, SV40 poly-A signal sequence, and the like.

Also, the elements required for the expression other than a promoter sequence or a transcription termination signal sequence in the expression unit include, for example, regulatory elements for efficiently expressing the objective gene including enhancer and IRES (internal ribosome entry site) sequence. The regulatory element may be arranged at a suitable site in the expression unit depending on its nature. These elements required for the expression are preferably selected in consideration of the combination with host and the productivity of the objective protein.

Also, the elements required for the expression may contain an intron sequence other than the objective protein gene in consideration of the increase of translation reaction. The intron sequence may be positioned between the transcription initiation site and transcription termination site in the expression unit, and preferably includes ones derived from virus and mammalian genome, which are preferably an intron sequence having a high splicing efficiency in an host.

Recombination of Multiple Copies of Expression Unit into Hprt Gene Locus

According to an embodiment of the present invention, it is suitable for the recombination of multiple copies of expression unit into the hprt gene locus to use a vector containing multiple copies of an expression unit. It is also possible to introduce a vector containing a single copy of an expression unit into a mammal cell for selecting and obtaining cells into which the multiple copies of the expression unit has been integrated, which is incorporated herein by reference. Furthermore, according to another embodiment of the present invention, it is also preferred to integrate a vector containing a marker gene for gene amplification and the expression unit of an objective protein gene into the hprt gene locus, and then to select cells into which the multiple copies of the expression unit has been integrated by gene amplification technology.

According to the preferred embodiment of the present invention, the expression unit of the objective protein gene is the one which has been integrated into the hprt gene locus by homologous recombination. The use of such homologous recombination is advantageous to the swift construction of a recombinant cell and further the stable expression of the objective protein gene at a high level.

Also, the site in the hprt gene locus as the target of homologous recombination may be appropriately established, unless efficient expression of the objective protein gene is prevented, for example, on the exon sequence such as exon 3 of the hprt gene. Establishment of a targeting region on the exon sequence inhibits the expression of the hprt gene itself and thus advantageous to efficient acquisition of the recombinant cell by drug selection with 6-thioguanine (6-TG) and azaguanine (8-AG).

Vector

The vectors used in the present invention include, but are not limited to, the ones which can integrate an objective gene into the chromosome of mammal cell such as plasmid vector, cosmid vector, phage vector, artificial chromosome vector, preferably, plasmid vector. Also, the vector may be comprised either linear or cyclic one.

The vector can be constructed with the standard method which is well known in the art, for example, according to the method described in Sambrook, J., et al., "Molecular Cloning: a laboratory manual", Cold Spring Harbor Laboratory Press, New York (1989).

When the expression unit is integrated into the hprt gene locus by homologous recombination, a homologous DNA sequence having homology which is capable of homologous recombination with a part of the hprt gene locus is disposed in the vector for integrating the expression unit. The homologous DNA sequences contained in the vector may be single or plural, and preferably two. Furthermore, the two homologous DNA sequences are preferably disposed in the 5'- and 3'-terminals. Thus, according to an embodiment of the present invention, the vector comprises at least a homologous DNA sequence disposed in the 5'-terminal, the expression unit of an objective protein gene and a homologous DNA sequence disposed in the 3'-terminal.

Also, the homologous DNA sequence has the homology and length which are capable of homologous recombination with hprt gene locus. In consideration of the feasibility or probability of the homologous recombination, the homologous DNA sequence and the hprt gene locus have preferably a homology of sufficiently high level, which is preferably in the range of 99% or more, more preferably 99.9% or more, and further preferably the both sequences are identical. In addition, these homologous DNA fragments have preferably a length of several hundred base pairs (bp) or more, more preferably 500 bp or more, and further preferably 1000 bp or more.

When a vector containing multiple copies of an expression unit is constructed, such vector is advantageously constructed by combining restriction enzyme reaction and ligation reaction. For instance, the type II restriction enzyme recognition sequences are disposed in both terminals of an expression unit to carry out reaction with the restriction enzyme for the recognition sequence, expendable DNA sequences such as operating sequence in *Escherichia coli* are removed by treatment such as gel excision, and the expression unit thus obtained is subjected to ligation reaction, so that a vector DNA in which multiple copies of expression unit are arranged in tandem can be constructed.

When all of the restriction enzyme recognition sequences are identical, a vector DNA in which multiple copies of an objective protein gene have random transcription directions can be constructed. Also, when different sequences are selected as the restriction enzyme recognition sequence, the direction of an objective protein gene in the DNA sequence can be controlled, and for example vector DNAs in which all of the objective protein genes are arranged in the same direction or the directions of the objective protein genes alternate with each other can be constructed.

The restriction enzyme which can be used may be the one which produces either a blunt end or a cohesive end, but it is preferably the restriction enzyme producing a cohesive end in consideration of the ligation efficiency. Also, in consideration of controlling the direction of the objective protein gene, a restriction enzyme having a variety of recognition sequences is preferably used, and for example includes type IIS restriction enzyme such as Sfi I restriction enzyme described in Biotech. Appl. Biochem., 20:157-171, 1994 or Japanese Patent Application Laid-Open disclosure No. 2003-530886. The Sfi I restriction enzyme, which will produce 64 different cohesive ends with use of one restriction enzyme, is preferred for controlling the directions of multiple copies of the objective protein genes, the entire disclosure of which are incorporated herein by reference.

The vector DNA containing multiple copies of the expression unit constructed by the ligation reaction may be purified, for example, by extraction with phenol-chloroform, and maintained in a host cell such as *E. coli* or yeast selected in consideration of the kind of the vector. In addition, when an appropriate host cell cannot be used, the vector DNA may be treated by extraction with phenol-chloroform and then introduced directly into mammal cells.

Also, in a vector for gene amplification, a marker gene for gene amplification is disposed in addition to the expression unit of the objective protein gene. The marker gene for gene amplification may be disposed in the neighborhood of the expression unit of the objective protein gene for the proper expression. Also, the expression unit of the objective protein gene may be contained either as a single copy or multiple copies.

In addition to those conditions described above, it is also possible to integrate marker genes (neomycin resistance gene, hygromycin resistance gene, zeocin resistance gene, puromycin resistance gene and the like) which are available for dominant selection with drug resistance into either vector described above in consideration of the selection of recombinant cells.

Process for Introducing Vector into Cell

Methods well known in the art may be used for introducing the vector into a mammal cell and include, for example, electroporation, microinjection, calcium phosphate transfection, and lipofection. Such transfer is appropriately selected by a person skilled in the art in consideration of mammal cell's species, vector sizes, transfer efficiencies, and the like. In this connection, when the vector is of a cyclic form, it may be linearized by a well known method before transfer into cell.

Selection of Recombinant Cell

Recombinant mammal cells can be selected and obtained by the methods such as drug selection well known in the art. For instance, if a plasmid vector containing the expression unit of an objective protein has a selective marker such as drug resistance gene which is available for dominant selection, recombinant cells can be selected and obtained by cell culture in a medium supplemented with the selection drug. Also when the objective protein gene is integrated in a site which blocks the expression of hprt gene, the recombinant mammal cell can be selected efficiently by adding 6-TG or 8-AG into a medium.

Furthermore, in the selection of a recombinant mammal cell, it is preferred to select accurately the recombinant cell containing multiple copies of the expression unit of the objective protein gene by using the genomic DNA assay of the recombinant cell by the PCR reaction or the Southern blot hybridization. It is also preferred to preliminarily culture the mammal cell in a HAT (hypoxanthine, aminopterin, thymidine) containing medium before vector transfer in consideration of the reduction of background level.

Integration of Multiple Copies by Gene Amplification

It is possible to obtain a recombinant cell having integrated multiple copies of an exogenous gene expression unit into the hprt gene locus by providing a recombinant cell wherein a vector containing an appropriate marker gene for gene amplification and an exogenous gene (preferably as an expression unit) has been integrated into the hprt gene locus and conducting an appropriate gene amplification process.

It is known in gene amplification technology that DNA sequences in the neighborhood of the gene amplification marker (ca. 10 kbp) are also amplified at the same time. Since the amplification occurs in the same chromosomal site, it is possible to increase the copy number of the objective protein gene within the hprt gene locus with use of gene amplification in this technique. Also, if gene amplification is employed, the orientations of the increased copies cannot be controlled, and thus a tandem arrangement having a uniform transcription direction of the expression units cannot always be obtained.

In the present invention, any of the well known marker genes for gene amplification may be used appropriately, and it is preferably dihydrofolate reductase gene (DHFR) or glutamine synthetase gene (GS), more preferably GS gene. In addition, it is appropriately employ as the gene amplification process the well known methods such as the screening of resistance cell in a medium having added thereto methotrexate (MTX) as a DHFR inhibitor and the screening in a medium having added thereto methionine sulfoximine (MSX) as a GS inhibitor. Furthermore, the well known methods in which the addition concentration of MTX or MSX is stepwise increased can be used more appropriately.

Recombinant Mammal Cell

Furthermore, the mammal cell according to the present invention is prepared by the aforementioned techniques and comprises multiple copies of an exogenous objective protein gene integrated into the hprt gene locus. In such recombinant mammal cell, the specific productivity level of the objective protein gene increases in proportion to its gene copies, and it is possible to maintain the specific productivity level stably over a long period of time.

Furthermore, the stable expression of the multiple copies of the objective protein gene for a long period is maintained even in the absence of selection drugs, so that it is advantageous to reducing the culturing cost as well as the cost of purification process which is carried out for avoiding the risk of pollution.

In addition, the copy number of the objective protein gene are in the range of 2 or more in the recombinant mammal cell. Also, according to an preferred embodiment of the present invention, the objective protein gene in the recombinant mammal cell comprises an expression unit which contains at least a promoter sequence and a transcription termination signal sequence and is integrated into the hprt gene locus. Also, the objective protein gene or the expression unit in the recombinant mammal cell may be integrated repeatedly in tandem. Moreover, according to an embodiment, the objective protein gene in the recombinant mammal cell is the one which has been integrated by homologous recombination.

Also, in the recombinant mammal cell according to the present invention, the specific productivity level of the objective protein increases depending on the copy number of the objective protein gene integrated into the hprt gene locus, and when the objective protein gene has 2 copies, the specific productivity level can be estimated about 0.4-20 pg/day per cell.

Also, in the recombinant mammal cell according to the present invention, the specific production level of the objective protein can be maintained for at least 97 days.

The stable expression of the objective protein gene for a long period is maintained even in the absence of selection drugs. The selection drug includes the well known drugs used in cell selection such as, for example, neomycin, 6TG, MTX, MSX, and the like.

Host Cell

Also, the mammal cell used as the host cell in the present invention is preferably the one derived from human, and the specific examples of the mammal cell include, for example, a HT1080 cell strain derived from human fibrosarcoma, but not limited thereto in consideration of the generality of the hprt gene in mammal.

Furthermore, when the objective protein gene is integrated into the hprt gene locus by homologous recombination, a host cell is preferably the one which has only one hprt gene locus in its whole genomes in consideration of the selection of homologous recombination cell with selection drugs such as 6TG and 8AG. Such cells include, for example, the aforementioned HT1080 strain, a cell strain having only one X chromosome derived from a male, and the like.

Culture/Isolation of Objective Protein

Also, in the process for producing the objective protein according to the present invention, a recombinant mammal cell wherein multiple copies of the objective protein gene have been integrated into the hprt gene locus can be cultured in a medium to produce the objective protein. The detailed condition for culturing the mammal cell is appropriately determined depending on the nature and state of the cell by a person skilled in the art, but the medium is preferably a serum-free medium, more preferably a chemically defined (CD) medium in consideration of culturing cost.

In addition, according to an embodiment of the present invention, the objective protein is preferably isolated from the culture of a recombinant mammal cell. As regards the isolation techniques, the well known techniques such as centrifugation, gel filtration and filtration via filter may be used depending on nature of the objective protein.

EXAMPLES

The present invention is now described specifically by reference to examples, but not limited thereto.

In this connection, conditions of reactions such as reaction with restriction enzyme, PCR reaction, ligation reaction, and the like have been established according to the reaction condition recommended by the maker or the method described in Molecular Cloning; 2nd edition, Sambrook et al., Cold Spring Harbor Laboratory Press. Furthermore, as regards a variety of plasmid vector DNA obtained and the like, the DNA sequence was determined with an automaticDNA Sequencer (310 Genetic Analyzer, Applied Bio Systems, Inc.).

Example 1

Production of Recombinant Cell Having Multiple Copies of Erythropoietin Gene Expression Unit Integrated in hprt Gene Locus 1

1-1: Construction of Plasmid Vector

In order to integrate multiple copies of erythropoietin (EPO) gene into the hprt gene locus, a vector (phprt-GT-EPO gene) containing a single copy of the EPO gene as represented in FIG. 1 was constructed in the following.

Acquisition of Homologous DNA Sequence

A human derived cell strain, HT1080 cell strain (JCRB Cell Bank, Cat. no: IFO50354) was treated with GFX(trade name) Genomic Blood DNA Purification Kit (Amersham Biosciences) to get a genomic DNA. Next, the genomic DNA was used as a template for the cloning of homologous DNA sequences (HA1 and HA2) of the targeting hprt gene by the PCR reaction (KOD-Plus-, TOYOBO). HA1 and HA2 were provided as sequences which are homologous to a region containing exon 3 of the hprt gene as illustrated also in FIG. 3. The primer sequences used in the PCR reaction are shown in the followings.

```
HA1 sense primer:
                                          (SEQ ID NO: 1)
5'-CCTGCAGGTCGCGATTGGTACTTGTTCAGCTTTATTCAAG-3'

HA1 antisense primer:
                                          (SEQ ID NO: 2)
5'-GTCGACAAGGACGCGTTCTGATAAAATCTACAGTCATAGGA-3'

HA2 sense primer:
                                          (SEQ ID NO: 3)
5'GTCGACCTCTAGCTAGAGCTTGGCGTAATCATGGTCTCCGGAGACTG

AAGAGCTATTGTGTGAGTAT-3'

HA2 antisense primer:
                                          (SEQ ID NO: 4)
5'-ACATGTTCTCTTAAGTCGCGAAGTAGTGTTATGATGTATGGGCA

TA-3'
```

In the PCR reaction, the recognition sites of restriction enzymes Sse 8387I and Nru I were added to the 5'-terminal of HA1 sense primer. Similarly, the recognition sites of Sal I and Mlu I were added to the 5'-terminal of HA1 antisense primer, the recognition sites of Sal I and Acc III to the 5'-terminal of HA2 sense primer, and the recognition sites of Pci I and Nru I to 5'-terminal of HA2 antisense primer, respectively.

A DNA sequence containing a replication origin in *E. coli* and an ampicillin resistance gene was subjected to cloning from DNA of pQBI25 plasmid vector (Wako Pure Chemical Industries, Ltd.) by the PCR reaction. The primer sequences used in the PCR reaction are shown in the following. In the PCR reaction, the recognition site of restriction enzyme Pci I was added to the 5'-terminal of the sense primer and the recognition site of restriction enzyme Sse 8387I was added to the 5'-terminal of the anti-sense primer.

```
E. coli sense primer:
                                        (SEQ ID NO: 5)
5'-ACATGTGAGCAAAAGGCCAGCAAAAGGCCAGGAAC-3'

E. coli antisense primer:
                                        (SEQ ID NO: 6)
5'-CCTGCAGGGACGTCAGGTGGCACTTTTCGGGGAAATGTGC-3'
```

HA1, HA2, and DNA sequence containing an ori sequence and an ampicillin resistance gene were subjected to cloning by PCR reaction, respectively. These three DNA sequences were cleaved with restriction enzymes Pci I, Sse 8387I and Sal I, and subjected to ligation reaction to obtain a pHA12 plasmid vector. Next, the pHA12 plasmid vector was cleaved with restriction enzymes Mlu I and Sal I to obtain DNA sequence 1 that HA2, the DNA sequence containing ori sequence and ampicillin resistance gene, and HA1 are linked in order from the 5'-terminal.

In addition, a pQBI25 plasmid vector was cleaved with restriction enzymes Not I and Sal I to obtain DNA sequence 2 (expression cassette containing SV40, neoR and SV40pA) containing a BGH poly-A signal sequence (BGH pA) and a neomycin resistance gene.

Furthermore, a pcDNA3.1 plasmid vector (Invitrogen) was cleaved with restriction enzymes Mlu I and Not I to obtain DNA sequence 3 containing a CMV promoter-enhancer sequence (CMV) and a multicloning site.

Next, the DNA sequences 1-3 were subjected to ligation to give a phprt-GT-MCS plasmid vector.

Next, an erythropoietin gene was amplified with a genomic DNA extracted from the HT1080 cell strain as a template by PCR reaction. The recognition sequence of the restriction enzyme Nhe I was added to the 5'-terminal of the sense primer, and the recognition sequence of restriction enzyme Eco RI to the 5'-terminal of the antisense primer. The primers have the following base sequences.

```
EPO gene as primer:
5'-CCTTGCTAGCATGGGGGTGCACGGTGAGTA-3' (SEQ ID NO: 7)

EPO gene as primer:
5'-CCTTGAATTCTCATCTGTCCCCTGTCCTGC-3' (SEQ ID NO: 8)
```

The EPO gene amplified by the PCR reaction and the phprt-GT-MCS plasmid treated with restriction enzymes Nhe I and Eco RI were ligated to insert the EPO gene between the Nhe I-Eco RI site of the multicloning site in the phprt-GT-MCS plasmid and to obtain a phprt-GT-EPO gene (9116 bp) shown in FIG. 1. The phprt-GT-EPO gene thus obtained was maintained in E. coli DH5α (New England Biolabs).

1-2: Vector Transfer into Cell
Linearization of Plasmid

Plasmid vector phprt-GT-EPO gene was purified with an Endofree Plasmid Maxi kit (QIAGEN), and cleaved with Nru I. It was dissolved in sterile water to a concentration of 2 g/L and used for the following transfection experiment.

Transfection

Human fibrosarcoma cell strain HT-1080 (JCRB Cell Bank ID: IFO50354) was prepared to a concentration of $1 \times 10^7$ cell/mL, and mixed with 2 μg of linearized plasmid vector phprt-GT-EPO gene. Next, with use of the mixture thus obtained, the phprt-GT-EPO gene was transfected into the cell strain HT-1080 by electroporation. The electroporation was conducted with Gene Pulser (BioRad) under the condition of 950 μF. Further particulars of this experiment was according to the condition described in Biotech. Bioeng., 2006, 95:1052-1060. The transfected cells were seeded at a concentration of 500 cells/well into a 96 well plate and cultured in an incubator at 37° C. in 5% $CO_2$ (medium: Advanced MEM (GIBCO) supplemented with 5% FBS and 1× Glutamax (GIBCO)), and G418 (Invitrogen) was added after 24 hours of transfection (final concentration: 500 μg/mL).

Screening

After culture for 8-12 days, it was confirmed that G418 resistance colonies appeared in the plate. At this step, fresh medium supplemented with 6TG (final concentration: 50 μM)(Wako Pure Chemical Industries, Ltd.) was added, and the mixture was further cultured for 8 days. After culture, all wells were checked, and 6TG resistance colonies were isolated.

1-3: Southern Blot Hybridization Assay/Acquisition of Objective Cell

In the following, Southern blot hybridization was conducted and the 6TG resistance colonies were screened to obtain a recombinant cell that multiple copies of EPO gene was integrated into the hprt gene locus.

Preparation of Probe

An NR probe having a sequence complementary to a neomycin resistance gene in the phprt-GT-EPO gene was synthesized as follows. First, the full-length of a neomycin resistance gene coding sequence was amplified by PCR and subjected to TA cloning into pGEM T plasmid vector (Promega). Next, a DIG (Digoxigein) labeled probe was prepared with a PCR DIG probe synthesis kit (Roche, primer: M13 Forward/Reverse Primer).

Preparation of Membrane

Each genomic DNA was extracted from the 6TG resistance colony with a GFX Genomic Blood DNA purification kit (Amersham Biosciences) and cleaved with Bgl II restriction enzyme. A 10 μg portion of cleaved genomic DNA was subjected to electrophoresis with 0.6% agarose gel, and blotted onto a nylon membrane (Hybond N+ membrane, Amaersham Biosciences). The membrane obtained was incubated at 80° C. for 2 hours to immobilize the DNA on the membrane.

Hybridization

The NR probe was hybridized on the membrane. At this time, prehybridization, hybridization and probe detection were carried out according to the DIG Application Manual (Roche). Also, the stripping of the probe was repeated twice with a stripping buffer (0.2M NaOH, 0.1% SDS) at 37° C. for 15 minutes.

As shown in FIG. 2, a DNA fragment of 15822 bp was detected in recombinant clone #14-5E with the NR probe. The recombinant clone was obtained as only one clone as a result of screening of about 30 clones. On the other hand, when a recombinant clone #19-3B was selected as a control, a DNA fragment of 8546 bp was detected.

The result of Example 1 is now described on the basis of the results illustrated in FIGS. 3(A)-(C) and FIG. 2.

As shown in FIG. 3(A), the targeting site (2) of homologous recombination of the hprt gene (1) is provided in a region containing exon 3 (3), and homology arm 1 (HA1) (4) and homology arm 2 (HA2) (5) are provided so as to be homologous to the two vicinal regions. In addition, the Bgl II restriction enzyme sites are positioned so as the targeting site (2) to be between the restriction enzyme sites, but not positioned within the targeting site. On the other hand, the Bgl II restriction enzyme site is not present in the DNA sequence (6) of phprt-GT-EPO gene illustrated in FIGS. 3(B) and (C). Also, the DNA sequence (6) of phprt-GT-EPO gene is designed so that the NR probe (7) can be hybridized.

As shown in FIG. 3(C), it was confirmed on the basis of the position of the Bgl II restriction enzyme site and the length of DNA sequence that the recombinant clone #14-5E from which a DNA fragment of 15822 bp was detected was the objective cell that two copies of the DNA sequence (6) of phprt-GT-EPO gene were repeatedly integrated in tandem.

On the other hand, as shown in FIG. 3(B), it was confirmed that the recombinant clone #19-3B as the control cell from which a DNA fragment of 8546 bp was detected was the one into which 1 copy of the DNA sequence (6) of phprt-GT-EPO gene was integrated.

Example 2

Study of EPO Specific Productivity 2-1: Culture of Recombinant Clone

Immediately after the establishment of the recombinant clones #14-5E and #19-3B, these clones were cultured in the absence of selection drugs G418 and 6TG.

Culture was conducted in an Advanced MEM (GIBCO) containing 5% FBS (Japan Bioserum) in the presence of 5% $CO_2$ at 37° C. Passage by treatment with trypsin was carried out at an interval of about 4-5 days at the time when cell number and cell density reached 70-80%. Cell counting and medium sampling were conducted at logarithmic growth phase periodically for the productivity assay of EPO in the following.

2-2: Sampling of Recombinant Clone and Medium

As regards the recombinant clones #14-5E and #19-3B cultured by the method described above, sample cells were obtained according to the following procedure.

First, cells were seeded at a concentration of $5\times10^4$ cells/dish and cultured in Advanced MEM (GIBCO) containing 5% of FBS (Japan Bio Serum) in the presence of 5% $CO_2$ at 37° C. On third and fourth day after initiation of culture (logarithmic growth phase), the medium was recovered, and furthermore, after recovering the medium, cells were treated with trypsin to recover the cells. The medium thus recovered was used in the following ELISA assay, and the cell number of the recombinant clones thus recovered was counted with a hematocytometer. In this connection, the trypsin treatment was performed with addition of 0.25% Trypsin-EDTA solution (GIBCO) at room temperature for 3 to 5 minutes. After trypsin treatment, reaction was terminated by adding a serum supplemented medium before recovering the cells.

2-3: ELISA

The amount of EPO accumulated in the medium thus recovered was assayed by determining the absorbance at 450 nm with Monoclonal anti-human EPO(R&D Systems) as an immobilized antibody, Polyclonal anti-human EPO(R&D Systems) as a primary antibody, and Anti-mouse Ig, horse-radish peroxidase linked whole antibody (from donkey) (Amersham Biosciences) as a secondary antibody in the presence of TMB No Hydrogen Peroxide 1 Component HRP Microwell substrate (BioFX).

2-4: Comparison of Specific Productivity of EPO Between Recombinant Clones #14-5E and #19-3B As regards the recombinant clones #14-5E and #19-3B just after establishment, the specific productivity of EPO per cell per day was calculated from the following equation based on accumulation amount of EPO in the recovered medium, number of cells and culturing time:

(specific productivity EPO)=(accumulation amount of EPO on 4th day-accumulation amount of EPO on 3rd day)/((number of cells on 3rd day+number of cells on 4th day)/2)/((culturing time between samplings)/24)

The result is shown in FIG. 4. In #14-5E containing two copies of EPO gene in the hprt gene locus, the specific productivity was 2.16 pg/cell/day. On the other hand, it was 1.17 pg/cell/day in #19-3B containing 1 copy of EPO gene. The EPO productivity of #14-5E clone was about twice as much as that of #19-3B clone, and the specific productivity level of EPO was increased additively in proportion to the copies integrated.

Example 3

Evaluation of the Effect of Long Period Culture in No Selection Drug Containing Medium 3-1: Determination of EPO Productivity The recombinant clone #14-5E was continuously cultured in a medium in the absence of G418 and 6TG for 97 days in the same manner as in Example 2. During the continuous culture, EPO productivity was periodically measured.

The result is shown in FIG. 5. In recombinant clone #14-5E, the specific productivity level of EPO was maintained constant for at least 97 days.

3-2: Southern Blot Hybridization

It was also confirmed by Southern blot hybridization according to the same manner as in Example 1 that whether two copies of EPO gene integrated in parallel into the hprt gene locus is maintained or not after culturing for a long period.

Figure 6:
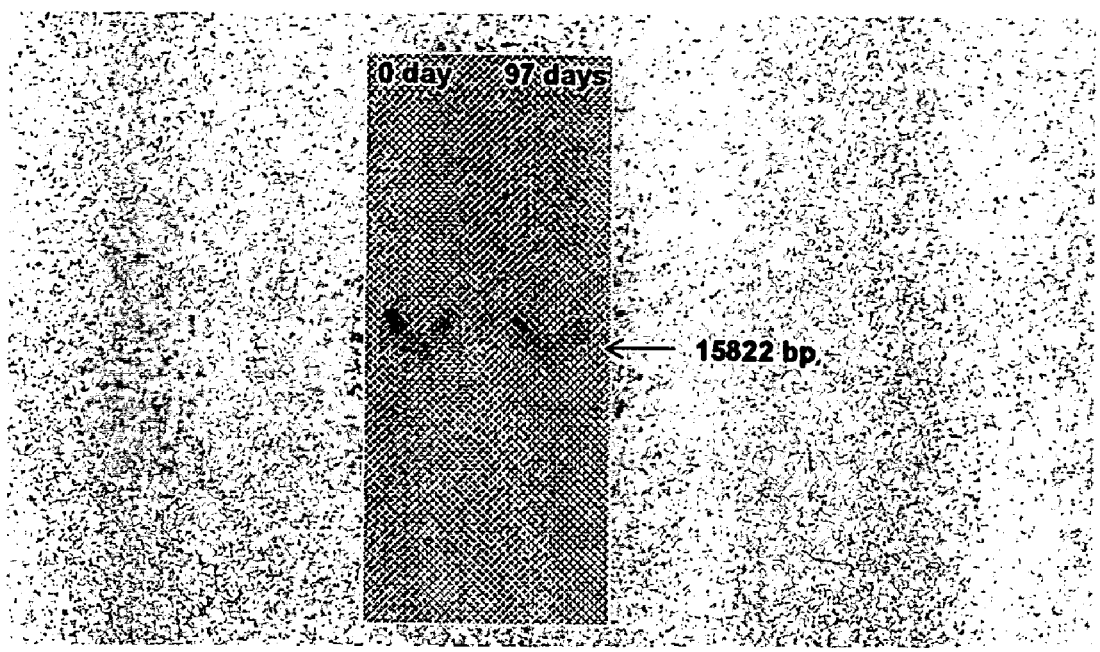
FIG. 6 is a photogram which illustrates the Southern blot hybridization in the recombinant clone (#14-5E) just before culture and cultured in a G418- and 6TG-free medium for 96 days.

As shown in FIG. 6, a DNA fragment of 15822 bp was detected at the initiation of culture (0 day) and after 97 days. It was confirmed that two copies of EPO gene sequence repeatedly integrated in tandem into the hprt gene locus was maintained stably for at least 97 days.

It was confirmed as shown in the above that the specific productivity level of EPO was increased additively together with the increase of the copy number of EPO gene in the cell strain wherein two copies of EPO gene was repeatedly integrated in tandem into the hprt gene locus and that the both was approximately in direct proportion. Furthermore, the reduction in the copy number of EPO gene, gene silencing or the decrease of specific productivity level were not observed also in continuous culture in the absence of selection pressure.

Example 4

Production of Recombinant Cell that Multiple Copies of Erythropoietin Gene Expression Units were Integrated into hprt Gene Vectors containing multiple copies of erythropoietin (EPO) gene (phprt-IVS-GT-EPO-2 and phprt-IVS-GT-EPO-3) were constructed to recombine efficiently multiple copies of EPO genes into the hprt gene according to the following procedure.

4-1: Construction of Plasmid Vector

Construction of Vector (phprt-IVS-GT-EPO-1) Containing 1 Copy of Erythropoietin Gene A vector containing 1 copy of EPO gene (phprt-IVS-GT-EPO-1) illustrated in FIG. 7 was first constructed as a construction material of a vector containing multiple copies of EPO gene according to the following procedure.

Plasmid phprt-GT-MCS was cleaved with restriction enzymes Eco RV and Apa I, treated with Klenow enzyme, and subjected to self-ligation reaction to give a plasmid phprt-GT-MCS that unnecessary restriction enzyme recognition sequence in MCS was removed.

Also, the cloning of a DNA fragment containing a CMV promoter-enhancer sequence and an intron sequence was conducted with a plasmid pIRES (BD Biosciences) as a template by PCR reaction to give PCR amplification products. Primer sequences used in the PCR reaction are shown below.

```
CMV-IVS-sense primer:
                 (SEQ ID NO: 9)
5'-CCTTACGCGTTCAATATTGGCCATTAGCCA-3'

CMV-IVS-antisense primer:
                 (SEQ ID NO: 10)
5'-CCTTGCTAGCCTATAGTGAGTCGTATTAAG-3'
```

Mlu I and Nhe I restriction enzyme recognition sequences were added to the 5'-terminals of the sense primer and the antisense primer, respectively. The plasmid phprt-GT-MCS was cleaved with restriction enzymes Nhe I and Mlu I and ligated to the PCR amplification products to give a plasmid phprt-IVS-GT-MCS.

Next, the cloning of the EPO cDNA sequence was conducted with the total RNA extracted from homologous recombinant HT1080 cell clone #19-3B as a template by RT-PCR reaction. Primer sequences used in the RT-PCR reaction are shown below.

```
EPO sense primer:
                 (SEQ ID NO: 11)
5'-CCTTGCTAGCATGGGGGTGCACGAATGTCC-3'

EPO gene as primer:
                 (SEQ ID NO: 8)
5'-CCTTGAATTCTCATCTGTCCCCTGTCCTGC-3'
```

Next, EPO cDNA was integrated at Nhe I and Eco RI restriction enzyme sites into the MCS of phprt-IVS-GT-MCS plasmid to construct a plasmid phprt-IVS-GT-EPO.

A DNA fragment which contains in order restriction enzyme sites Bgl II, Not I, Xba I, and Apa I from the 5'-terminal side was ligated between unique restriction enzyme sites (Acc III and Sal I) which are present between neomycin resistance gene unit and HA2 in the plasmid phprt-IVS-GT-EPO to give a plasmid phprt-IVS-GT-EPO-1 illustrated in FIG. 7. The plasmid phprt-IVS-GT-EPO-1 was used in the construction of a vector containing multiple copies of EPO gene.

Construction of Vector Containing Two Copies of Erythropoietin Gene (phprt-IVS-GT-EPO-2)

Next, a vector containing two copies of erythropoietin gene (phprt-IVS-GT-EPO-2) illustrated in FIG. 8 was constructed according to the following procedure.

First, the plasmid phprt-IVS-GT-EPO was cleaved with restriction enzymes Sal I and Mlu I, and a sequence containing an EPO gene expression unit from which HA1, HA2, and an operation sequence within *E. coli* was removed was obtained from the plasmid thus obtained. Next, Two operation sequences within *E. coli* were obtained with a pQBI25 plasmid vector (Wako Pure Chemical Industries, Ltd.) as a template by the PCR reaction with an *E coli*-B sense primer and an *E coli*-N antisense primer and the PCR reaction with an *E coli*-X sense primer and an *E coli*-A antisense primer.

Each of the two operation sequences was ligated to the sequence containing the EPO gene expression unit to give an EPO-BN plasmid which contained Bgl II and Not I restriction enzyme recognition sequences at the both terminals and an EPO-XA plasmid which contained Xba I and Apa I restriction enzyme recognition sequences at the both terminals, respectively.

```
Ecoli-B sense primer:
           (for Bgl II site: SEQ ID NO: 12)
5'-CTACGCGTAGATCTGACGTCAGGTGGCACT-3'

Ecoli-N antisense primer:
           (for Not I site: SEQ ID NO: 13)
5'-CTGTCGACGCGGCCGCACATGTGAGCAAAA-3'

Ecoli-X sense primer:
           (for Xba I site: SEQ ID NO: 14)
5'-CTACGCGTTCTAGAGACGTCAGGTGGCACT-3'

Ecoli-A antisense primer:
           (for Apa I site: SEQ ID NO: 15)
5'-CTGTCGACGGGCCCACATGTGAGCAAAAGG-3'
```

Next, the plasmids phprt-IVS-GT-EPO-1 and EPO-BN were cleaved with restriction enzymes Bgl II and Not I, respectively, and subjected to ligation to give a plasmid phprt-IVS-GT-EPO-2 in which two copies of the EPO gene expression unit arranged in the same direction were contained repeatedly (FIG. 8).

Construction of Vector Containing Three Copies of Erythropoietin Gene (phprt-IVS-GT-EPO-3)

Next, the plasmids phprt-IVS-GT-EPO-2 and EPO-XA were cleaved with restriction enzymes Xba I and Apa I, respectively, and subjected to ligation to give a plasmid phprt-IVS-GT-EPO-3 in which three copies of the EPO gene expression unit arranged in the same direction were contained repeatedly (FIG. 9).

In this connection, the phprt-IVS-GT-EPO-1, phprt-IVS-GT-EPO-2 and phprt-IVS-GT-EPO-3 were maintained in *E. coli* DH5α (New England Biolabs), respectively.

4-2: Introduction of Vector into Cell

Linealization of Plasmid

The plasmid vectors phprt-IVS-GT-EPO-2 and phprt-IVS-GT-EPO-3 containing multiple copies of EPO genes were purified with Endofree Plasmid Maxi kit (QIAGEN), cleaved with Nru I, and dissolved in sterile water to a concentration of 2 g/L, which was used for the following transfection experiment.

Transfection and Screening

Linealized plasmid vectors phprt-IVS-GT-EPO-2 and hprt-IVS-GT-EPO-3 were introduced into a human fibrosarcoma cell strain HT-1080 (JCRB Cell Bank ID: IFO50354) to obtain a homologous recombination cell strain. Transfection and screening were performed under the same condition described in Example 1.

Three colonies having resistance against G418 and 6TG were obtained by the transfection of phprt-IVS-GT-EPO-2. On the other hand, one colony having resistance against G418 and 6TG was obtained by electroporations twice under the same condition in the transfection of phprt-IVS-GT-EPO-3.

4-3: Assay by Genomic PCR

A genomic DNA was extracted from the colony having resistance against G418 and 6TG which was obtained by the transfection of phprt-IVS-GT-EPO-2 and phprt-IVS-GT-EPO-3 with a GFX Genomic Blood DNA purification kit (Amersham Biosciences), and site-specific recombination into a targeting hprt gene locus was confirmed by the following PCR reaction with the genomic DNA. In this connection, the phprt-IVS-GT-EPO-1 containing a single copy of EPO gene as a reference was also subjected to linearization, transfection and screening in the same manner as phprt-IVS-GT-EPO-2 and phprt-IVS-GT-EPO-3 for the assay by genomic PCR.

Figure 10:
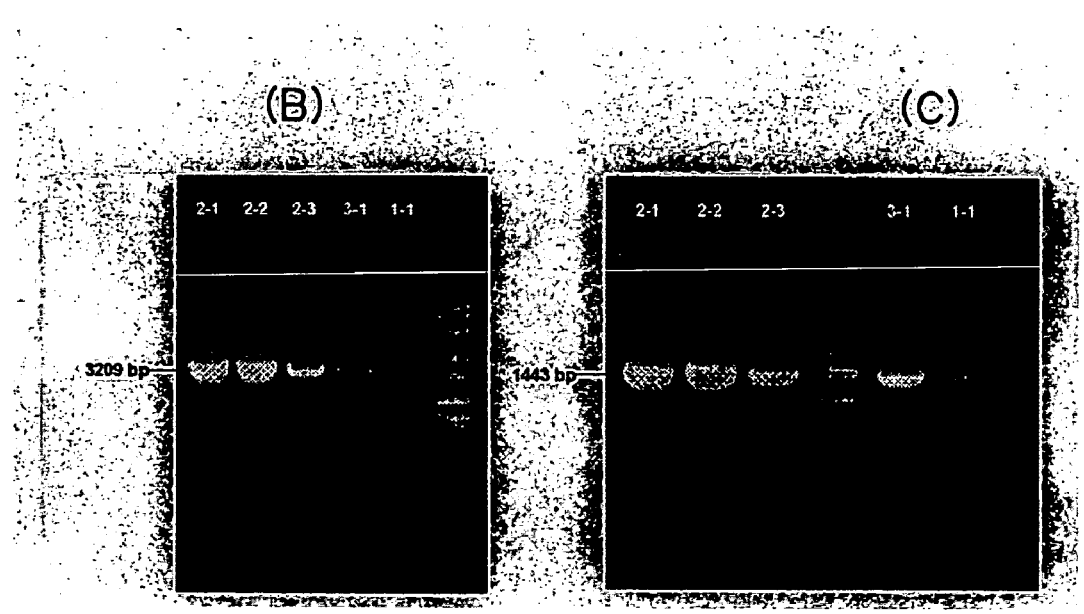
FIG. 10(A) is a schematic view which illustrates in detail the analysis of homologous recombination by genomic PCR; (B) is a photogram which illustrates the electrophoresis data for genomic PCR products, using DNA sequence (3209 bp) around the homology arm region of the transferred vector as an index; and (C) is a photogram which illustrates the electrophoresis data for genomic PCR products, using DNA (1443 bp) sequence around the homology arm region of the transferred vector as an index.

FIG. 10(A) is a schematic view which illustrates particularly the assay of homologous recombination reaction with genomic PCR. The targeting site (2) of homologous recombination in hprt gene(1) is provided as the one containing exon 3 (3). From the vector DNA (8), HA1 (4), HA2 (5) and a repeated sequence (9) containing EPO expression unit, which is interposed between the arms, are integrated into this region by homologous recombination. In this connection, n means the number of repeated sequences containing EPO expression unit and represents 1-3 in Example 4.

DNA sequences which contain HA1 (4) or HA2 (5) and a part of the repeated sequence (9) containing the EPO expression unit (DNA sequences of 3209 bp and 1443 bp) can be obtained from the homologously recombinated genome, and these sequences will be an index of homologous recombination.

Thus, the DNA sequence of 3209 bp illustrated in FIG. 10(A) was provided as an index of the homologous recombination of HA1 and the targeting site, and the DNA sequence was detected by PCR reaction with primers HPRTs2/Bgh-sc described below. On the other hand, another DNA sequence of 1443 bp illustrated in FIG. 10(A) was provided as an index of the homologous recombination of HA2 and the targeting hprt gene locus, and the DNA sequence was detected by PCR reaction with primers HPRTs1/Neo-seqSC described below.

```
HPRTs2 primer:
                                   (SEQ ID NO: 16)
5'-AAAGTTCTCTCCTTTCAGCCTTCTGTACAC-3'

Bgh-sc primer:
                                   (SEQ ID NO: 17)
5'-GCACCTTCCAGGGTCAAGGA-3'

HPRTas1 primer:
                                   (SEQ ID NO: 18)
5'-ACAAGTTAAAAGGAGCTTATGGGTAGGAAG-3'

Neo-seqSC primer:
                                   (SEQ ID NO: 19)
5'-CCTTCTATCGCCTTCTTGAC-3'
```

Next, PCR amplification products thus obtained was assayed by electrophoresis on 1.0% agarose gel. The results are shown in FIGS. 10(B) and (C).

In FIGS. 10(B) and (C), 2-1, 2-2 and 2-3 represent clones obtained with the phprt-IVS-GT-EPO-2 plasmid vector, 3-1 represents a clone obtained with the phprt-IVS-GT-EPO-3 plasmid vector, and 1-1 represents a clone obtained with the phprt-IVS-GT-EPO-1 plasmid vector. In all of the clones obtained were confirmed the PCR amplification products of 3209 bp and 1443 bp indicating the homologous recombination reaction.

As described above, when a vector containing multiple copies of EPO gene (phprt-IVS-GT-EPO-2 or phprt-IVS-GT-EPO-3) was used, recombinant cell clone having integrated two copies thereinto appeared in a frequency of 3 clones per electroporation, and clone having integrated three copies thereinto appeared in a frequency of 1 clone per 2 electroporation operations.

Example 5

Production of Recombinant Cell that One Copy of epo Gene Expression Unit and gs Gene Amplification Marker have been Integrated into hprt Gene Locus 5-1: Construction of Plasmid Vector A vector illustrated in FIG. 11 (pSV-GS-neo-GT-EPO #22) was constructed hereafter in order to integrate an erythropoietin (EPO) gene and a glutamine synthetase (GS) gene amplification marker into the hprt gene locus.

Construction of Basic Framework of Vector

A PCR amplification product 1 of a neomycin resistance gene coding sequence containing a Sma I restriction enzyme site at 5'-terminal and a Not I restriction enzyme site at 3'-terminal was obtained by PCR reaction with NEO-ss primer, NEO-as primer and a commercially available pIRES vector (BD Biosciences) as a template. The PCR amplification product 1 and the pIRES vector were cleaved with restriction enzymes Sma I and Not I, and subjected to ligation reaction to give a plasmid 1. The primer sequences used in the PCR reaction are shown in the following.

```
NEO-ss primer:
                                   (SEQ ID NO: 20)
5'-CCTTCCCGGGATGATTGAACAAGATGGAT-3'

NEO-as primer:
                                   (SEQ ID NO: 21)
5'-CCTTGCGGCCGCTCAGAAGAACTCGTCA-3'
```

Next, a PCR amplification product 2 containing a Sal I restriction enzyme site at 5'-terminal and a Bam HI restriction enzyme site at 3'-terminal was obtained by PCR reaction with BGH-ss primer, BGH-as primer and a pQBI25 vector (Wako Pure Chemical Industries, Ltd.) as a template. In the similar manner, a PCR amplification products 3 containing a Stu I restriction enzyme site at 5'-terminal and a Sal I restriction enzyme site at 3'-terminal was obtained by PCR reaction with an MCS-ss primer, an MCS-as primer and a PIRES vector as a template. The primer sequences used in the PCR reaction are shown in the following.

```
BGH-ss primer:
                                   (SEQ ID NO: 22)
5'-GTCGACGATATCTCTAGATGTGCCTTCTAG-3'

BGH-as primer:
                                   (SEQ ID NO: 23)
5'-CCTTGGATCCTCCGGAAGCCATAGAGCCCA-3'

MCS-ss primer:
                                   (SEQ ID NO: 24)
5'-CCTTAGGCCTAGGCTTTTGCAAAAAGCTTTATTGCGGTAGT-3'

MCS-as primer:
                                   (SEQ ID NO: 25)
5'-TCTAGAGATATCGTCGACCTATAGTGAGTC-3'
```

The plasmid 1 described above was cleaved with restriction enzymes Stu I and Bam HI to give cleaved fragments of 991 bp and 5876 bp. The cleaved fragment of 5876 bp was purified by agarose gel electrophoresis and gel excision operation to give DNA fragment 1. Also, the PCR amplification product 2 was cleaved with restriction enzymes Sal I and Bam HI to give DNA fragment 2. In the similar manner, the PCR amplification product 3 was cleaved with restriction enzymes Stu I and Sal I to give DNA fragment 3. The DNA fragments 1-3 were subjected to ligation to give plasmid 2.

A PCR amplification product 4 containing a Sal I restriction enzyme site at 5'-terminal and a Xba I restriction enzyme site at 3'-terminal of a GS coding sequence was obtained by RT-PCR reaction with a GS-ss primer, a GS-as primer and total RNA as a template which was extracted with ISOGEN (NIPPON GENE) from a human derived cell strain, HT1080 cell strain (Cat. no: IF050354) obtained from JCRB Cell Bank. A One Step RT-PCR Kit (QIAGEN) was used in the RT-PCR reaction. In addition, a PCR amplification product 5 containing a Nhe I restriction enzyme site at 5'-terminal and a Eco RI restriction enzyme site at 3'-terminal of an epo gene was obtained by PCR reaction with an EPO-ss primer, an EPO-as primer and a genomic DNA as a template which was extracted from the human HT1080 cell strain with GFX™ Genomic Blood DNA Purification Kit (Amersham Biosciences). The primer sequences used in the PCR reaction are shown in the following.

```
GS-ss primer:
                                    (SEQ ID NO: 26)
5'-CCTTGTCGACCACCATGACCACCTCAGCAA-3'

GS-as primer:
                                    (SEQ ID NO: 27)
5'-CCTTTCTAGATTAATTTTTGTACTGGAAGG-3'

EPO-ss primer:
                                    (SEQ ID NO: 28)
5'-CCTTGCTAGCATGGGGGTGCACGGTGAGTA-3'

EPO-as primer:
                                    (SEQ ID NO: 29)
5'-CCTTGAATTCTCATCTGTCCCCTGTCCTGC-3'
```

The plasmid 2 and the PCR amplification product 4 were cleaved with restriction enzymes Sal I and Xba I, and subjected to ligation to give plasmid 3. Next, the plasmid 3 and the PCR amplification product 5 were cleaved with restriction enzymes Nhe I and Eco RI, and subjected to ligation to give a plasmid 4 containing an EPO expression unit and a gs amplification marker.

Acquisition of Homologous DNA Sequence

Figure 12:
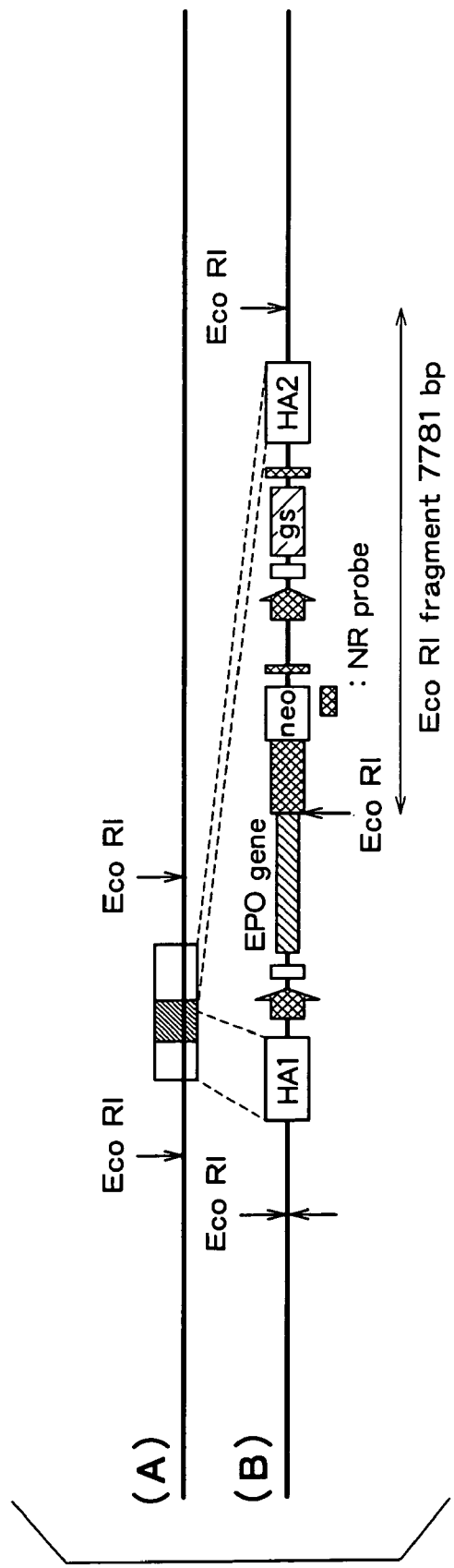
FIG. 12 (A) illustrates the targeting site of homologous recombination in the hprt gene locus; and (B) illustrates a schematic view in which 1 copy of DNA sequence for introducing pSV-GS-neo-GT-EPO #22 has been integrated into the genomic DNA of a clonic cell by homologous recombination.

Targeting homologous DNA sequences (HA1 and HA2) of the hprt gene were subjected to cloning by PCR reaction (KOD-Plus-, TOYOBO) with genomic DNA of the HT1080 strain. HA1 and HA2 were designed as a sequence homologous to a region containing exon 3 of the hprt gene as shown in FIG. 12. The primer sequences used in the PCR reaction are shown in the following.

```
HA1 sense primer:
                                    (SEQ ID NO: 1)
5'-CCTGCAGGTCGCGATTGGTACTTGTTCAGCTTTATTCAAG-3'

HA1-SB antisense primer:
                                    (SEQ ID NO: 30)
5'-GTCGACAAGGAGATCTACGCGTTCTGATAAAATCTACAGTCATAG
GA-3'

HA2 sense primer:
                                    (SEQ ID NO: 3)
5'-GTCGACCTCTAGCTAGAGCTTGGCGTAATCATGGTCTCCGGAGACTG
AAGAGCTATTGTGTGAGTAT-3'

HA2 antisense primer:
                                    (SEQ ID NO: 4)
5'-ACATGTTCTCTTAAGTCGCGAAGTAGTGTTATGATGTATGGGCA
TA-3'
```

In the PCR reaction, the recognition site of restriction enzymes Sse 8387I and Nru I were added to the 5'-terminal of HA1 sense primer. In the similar manner, the recognition site of Sal I and Bgl II was added to the 5'-terminal of HA1 antisense primer, the recognition site of Sal I and Acc III to the 5'-terminal of HA2 sense primer, and the recognition site of Pci I and Nru I to the 5'-terminal of HA2 antisense primer, respectively.

A DNA sequence containing a replication origin in *E. coli* and an ampicillin resistance gene was subjected to cloning from DNA of pQBI25 plasmid vector by the PCR reaction. The primer sequences used in the PCR reaction are shown in the following. In the PCR reaction, the recognition site of restriction enzyme Pci I was added to the 5'-terminal of the sense primer and the recognition site of restriction enzyme Sse 8387I was added to the 5'-terminal of the antisense primer.

```
E. coli sense primer:
                                    (SEQ ID NO: 5)
5'-ACATGTGAGCAAAAGGCCAGCAAAAGGCCAGGAAC-3'

E. coli antisense primer:
                                    (SEQ ID NO: 6)
5'-CCTGCAGGGACGTCAGGTGGCACTTTTCGGGGAAATGTGC-3'
```

HA1, HA2, and a DNA sequence containing an ori sequence and an ampicillin resistance gene were subjected to cloning by the PCR reaction. These three DNA sequences were cleaved with restriction enzymes Pci I, Sse 8387I and Sal I, and subjected to ligation reaction to give pHA12 plasmid vector. Next, the pHA12 plasmid vector was cleaved with restriction enzymes Bgl II and Acc III to give a DNA sequence 1 in which HA2, a DNA sequence containing an ori sequence and an ampicillin resistance gene, and HA1 were linked in order from the 5'-terminal.

Plasmid 4 containing an EPO expression unit and a gs amplification marker was cleaved similarly with restriction enzymes Bgl II and Acc III to give cleaved fragments of about 2 kbp and about 6.2 kbp. Purification was performed by agarose gel electrophoresis and gel excision operation to give a fragment of about 6.2 kbp. This fragment was subjected to ligation to the DNA sequence 1 to give a vector pSV-GS-neo-GT-EPO #22 illustrated in FIG. 11. The vector pSV-GS-neo-GT-EPO #22 thus obtained was maintained in *E. coli* DH5α (New England Biolabs).

5-2: Introduction of Vector into Cell

Linearization of Plasmid

The plasmid vector pSV-GS-neo-GT-EPO #22 was purified with a Endofree Plasmid Maxi kit (QIAGEN) and cleaved with Nru I. After purification by phenol-chloroform extraction, the vector was dissolved in sterile water to a concentration of 2 g/L for use in the following transfection experiment.

Transfection

Human fibrosarcoma cell strain HT-1080 (JCRB Cell Bank ID: IFO50354) was prepared in a concentration of $1 \times 10^7$ cells/mL, and mixed with 2 μg of linearized plasmid vector pSV-GS-neo-GT-EPO #22. Next, the mixture obtained was subjected to electroporation for the transfection of pSV-GS-neo-GT-EPO #22 into the cell strain HT-1080. Electroporation was performed with GenePulser (BioRad) under the condition of 950 μF. Further details of the experiment were according to the condition described in Biotech. Bioeng., 2006, 95:1052-1060. The transfected cells were seeded at a concentration of 500 cells/well into a 96 well plate and cultured in an incubator at 37° C. in 5% $CO_2$ (medium: Advanced MEM (GIBCO) supplemented with 5% FBS and 1× Glutamax (GIBCO)), and G418 (Invitrogen) was added after 24 hours of transfection (final concentration: 500 µg/mL).
Screening After culturing for 8-12 days, it was confirmed that G418 resistance colonies appeared in the plate. At this step, fresh medium supplemented with 6TG (final concentration: 50 µM)(Wako Pure Chemical Industries, Ltd.) was added, and the mixture was further cultured for 8 days. After culturing, all wells were checked, and 6TG resistance colonies were isolated.
5-3: Southern Blot Hybridization Assay In the following, screening of 6TG resistance colony was carried out by Southern blot hybridization.
Preparation of Probe An NR probe having a sequence complementary to a neomycin resistance gene in the pSV-GS-neo-GT-EPO #22 gene was synthesized as follows. First, the full-length of a neomycin resistance gene coding sequence in the pSV-GS-neo-GT-EPO #22 was amplified by PCR and subjected to TA cloning into pGEM T plasmid vector (Promega). Next, a DIG (Digoxigein) labeled probe was prepared with a PCR DIG probe synthesis kit (Roche, primer: M13 Forward/Reverse Primer).
Preparation of Membrane Each genomic DNA was extracted from the 6TG resistance colony with a genomic prep cells and tissue DNA isolation kit (Amersham Biosciences) and cleaved with restriction enzyme Eco RI. A 10 µg portion of cleaved genomic DNA was subjected to electrophoresis with 0.6% agarose gel, and blotted onto a nylon membrane (Hybond N+ membrane, Amaersham Biosciences). The membrane obtained was incubated at 80° C. for 2 hours to immobilize the DNA on the membrane.
Hybridization The NR probe was hybridized on the membrane. At this time, prehybridization, hybridization and probe detection were carried out according to the DIG Application Manual (Roche).

As shown in FIG. 13, a DNA fragment of about 8 kbp was detected in recombinant clones 118S, 118S-2, 118S-3 and 118S-5 with the NR probe. The site of restriction enzyme Eco RI is present in pSV-GS-neo-GT-EPO #22 and the targeting hprt gene locus respectively. A Eco RI fragment of 7781 bp is detected with the NR probe when homologous recombination reaction is successfully done. This result indicates that all of the 4 clones illustrated in FIG. 13 are recombinant cells that 1 copy of an epo gene expression unit and gs gene amplification marker have been integrated into the targeting hprt gene locus.

Example 6

Production of Recombinant Cell that Multiple Copies of epo Gene Expression Units have been Integrated into Hprt Gene Locus by Gene Amplification 6-1: Study of Proliferation Ability in Glutamine-Free Medium Prior to the screening of a gene amplification cell by the addition of MSX into a medium, proliferation ability in glutamine-free medium was evaluated. The cell clone maintained in a medium supplemented with glutamine (medium composition: Advanced MEM supplemented with 5% FBS and 1× Glutamax) was treated with trypsin at a stage of 70-80% confluence to recover the cells. The cell density of the recovered cell suspension was determined by Trypan blue staining. Cells were seeded in a concentration of $1.7 \times 10^5$ cells/culture dish (diameter: 10 cm), and 10 ml of glutamine-free medium (medium composition: Advanced MEM supplemented with 2% FBS and 1×GS supplement (NICHIREI)) was added for culture in a $CO_2$ incubator. After culturing for 6 days, cells were recovered in the same procedure, and the total number of cells was calculated from the amount and cell density of the recovered cell suspension to evaluate the proliferation ability of the cell. In the same procedure, $1.7 \times 10^5$ cells were placed in a new culture dish, and 10 ml of glutamine-free medium was added for culture in a $CO_2$ incubator. This operation was repeated twice to examine the proliferation in glutamine-free medium.
Selection of Acclimated Clone During the third culture period, increase of cell proliferations to two- and four-folds were observed in clone 118S-2 and 118S-5, respectively, while no proliferation was observed in non-recombinant HT1080 cell. Thus, these two clones were believed that proliferation in a glutamine-free medium is supported by the expression of exogenous gs gene. 118S-5 clone which was proliferated most successfully was used in the following MSX screening.
6-2: MSX Screening Clone 118S-5 maintained in a medium supplemented with glutamine was treated with trypsin at a stage of 70-80% confluence to recover the cells. Cell suspensions in a concentration of $1 \times 10^4$ cells/ml and $2 \times 10^4$ cells/ml were prepared with a selection medium (medium composition: Advanced MEM supplemented with 2% FBS, 1×GS supplement, 5 or 10 µM MSX) of which MSX concentration was adjusted to 5 or 10 µM. The cell suspension was seeded on a 96 well microtest plate (BD Falcon) in an amount of 100 µL/well, and cultured at 37° C. under 5% $CO_2$. After a week of culture initiation, the medium was changed into a fresh one. After culturing for a week further, wells in which proliferation was observed were distinguished by microscopic observation. In the selection medium in which MSX concentration was set up at 10 µM, no resistant cells were observed, and thus no wells in which cell proliferation was observed were found. On the other hand, resistant cells were observed in about 30% of well having seeded the cell suspension therein in the selection medium in which MSX concentration was set up at 5 µM. Next, the amount of EPO accumulated in these wells was determined by ELISA.
6-3: Selection of Gene Amplification Cells Depending on the Production Amount of EPO
ELISA Assay was performed by determining the absorbance at 450 nm with Monoclonal anti-human EPO(R&D Systems) as an immobilized antibody, Polyclonal anti-human EPO(R&D Systems) as a primary antibody, and Anti-mouse Ig, horseradish peroxidase linked whole antibody (from donkey) (Amersham Biosciences) as a secondary antibody in the presence of TMB, No Hydrogen Peroxide 1 Component HRP Microwell substrate (BioFX).
Assay of the Accumulated Amount of EPO Two days before determination of the accumulated amount of EPO by ELISA, the selection medium in a 96 well plate in which resistant cells were present was completely changed into a fresh one. The medium was recovered in an amount of 50 µL/well and determination was conducted by ELISA. As a result, EPO was accumulated in an amount of 0.3-37 ng/ml in culture for 2 days. Next, the clones 2-1F8 of which the accumulated amount of EPO showed the maximum of 37.3 ng/ml and 1-2E6 of which the accumulated amount of EPO showed the medium of 17.7 ng/ml were subjected to assay of the copy number of gs gene.

6-4: Assay of the Copy Number of gs Gene

Preparation of Genomic Samples

Extraction of genome from cell was carried out with a DNA Isolation kit for cells and tissues (Roche). The extracted genome was cleaved with a restriction enzyme Hind III (TaKaRa), and then genome was recovered by ethanol precipitation and dissolved in sterile water. DNA concentration was determined by measuring absorbance.

Real-Time Quantitative PCR Assay

The copy number of gs gene as an amplification marker was determined by real-time quantitative PCR with genomic DNA. Real-time quantitative PCR was carried out on ABI PRISM 7300 (ABI) with Taqman Universal PCR Master Mix (ABI). The sequences of primers and a probe used in the PCR reaction are shown in the following.

```
hGS For primer:
5'-ACCCCTTTTCGGTGACAGAA-3'   (SEQ ID NO: 31)

hGS Rev primer:
5'-TCGCCGGTTTCATTGAGAAG-3'   (SEQ ID NO: 32)

hGS cDNA-Taqman probe:
5'-CCCTCATCCGCACGTG-3'       (SEQ ID NO: 33)
```

Copy Number Analysis

The results of quantitative PCR were analyzed with an accessory 7300 system software. The copy number was calculated according to the following procedure. The copy number was calculated from the Ct values measured with the hGS primer and the probe for each genome sample and a calibration curve of a vector having a known concentration (pSV-GS-neo-GT-EPO#22). The copy number of beta-actin as the other site in the genome was further measured in order to correct the amount of genome in each sample, and the correction was performed so as the value to be constant.

The result is illustrated in FIG. 14. Cells 2-1F8 and 1-2E6 are the ones which were obtained from the clone 118S-5 and exhibit resistance against 5 μM of MSX. The cell S-5 (Glu−) is the clone 118S-5 maintained in a glutamine-free medium. The cell S-5 (Glu+) is the clone 118S-5 maintained in a medium supplemented with glutamine. The relative values of copy numbers in each cell assayed by Realtime PCR were calculated on the basis of S-5 (Glu+) as a control, and the result is illustrated as copy number ratios in the bar graph. The cell 2-1F8 showed a ratio of 2.67, and the cell 1-2E6 showed a ratio of 1.43. It can be concluded from these results that the cell 2-1F8 as an MSX resistance cell strain has an increased copy number by gene amplification. In consideration of the principle of gene amplification technology, the cell can be concluded as a cell strain of which copy number has been increased in the neighborhood of integration site. Also, the amount of accumulated EPO by ELISA assay is 37.3 ng/ml in the cell 2-1F8 and 17.7 ng/ml in the cell 1-2E6, which are correlated with the values of copy number.

What is claimed is:

1. A method of producing an objective protein comprising providing a mammal cell having an exogenous objective protein gene integrated into a hypoxanthine-phosphoribosyl transferase enzyme (hprt) gene locus and having a marker gene for gene amplification integrated thereinto wherein the marker gene is glutamine synthetase gene (GS), subjecting said cell to a condition to cause gene amplification thereby increasing the copy number of the exogenous objective protein gene integrated into the hprt gene locus to obtain a recombinant mammal cell having multiple copies of the exogenous objective protein gene integrated into the hprt gene locus, wherein the condition to cause gene amplification is a process of screening resistance cell in a medium comprising methionine sulfoximine (MSX) as a GS inhibitor and, culturing said cell to produce said objective protein.

2. The method according to claim 1, wherein said objective protein gene has a copy number of 2 or more.

3. The method according to claim 1, wherein said objective protein gene is integrated as an expression unit containing at least a promoter sequence and a transcription termination signal sequence into the hprt gene locus.

4. The method according to claim 1, wherein said objective protein gene or said expression unit is integrated repeatedly in tandem.

5. The method according to claim 1, wherein a host cell is a cell derived from human.

6. The method according to claim 5, wherein said host cell is a cell strain HT1080 derived from human fibrosarcoma.

7. The method according to claim 1, wherein said cell is cultured in the absence of a selecting drug.

8. The method according to claim 1, wherein the concentration of MSX is stepwise increased.

9. A method of producing a mammal cell in which multiple copies of exogenous protein gene are integrated into the hprt gene locus, comprising providing a cell having the exogenous objective protein gene integrated into the hprt gene locus and having a marker gene for gene amplification integrated thereinto wherein the marker gene is glutamine synthetase gene (GS), and subjecting said cell to the condition of causing gene amplification to increase the copy number of exogenous objective protein gene integrated into the hprt gene locus wherein the condition of causing gene amplification is a process of screening resistance cell in a medium having added thereto methionine sulfoximine (MSX) as a GS inhibitor.

10. The method according to claim 9, wherein the concentration of MSX is stepwise increased.

11. A mammal cell in which multiple copies of exogenous protein gene are integrated into the hprt gene locus, the cell being produced by a method comprising providing a mammal cell having an exogenous objective protein gene integrated into a hypoxanthine-phosphoribosyl transferase enzyme (hprt) gene locus and having a marker gene for gene amplification integrated thereinto wherein the marker gene is glutamine synthetase gene (GS), subjecting said cell to a condition to cause gene amplification thereby increasing the copy number of the exogenous objective protein gene integrated into the hprt gene locus, wherein the condition to cause gene amplification is a process of screening resistance cell in a medium comprising methionine sulfoximine (MSX) as a GS inhibitor.

12. The cell according to claim 11, wherein said objective protein gene has a copy number of 2 or more.

13. The cell according to claim 11, wherein said objective protein gene is integrated as an expression unit containing at least a promoter sequence and a transcription termination signal sequence into the hprt gene locus.

14. The cell according to claim 11, wherein said objective protein gene or said expression unit is integrated repeatedly in tandem.

15. The cell according to claim 11, wherein a host cell is a cell derived from human.

16. The cell according to claim 15, wherein said host cell is a cell strain HT1080 derived from human fibrosarcoma.

17. A method of producing the cell according to claim 11, comprising a step of integrating multiple copies of exogenous objective protein gene into the hprt gene locus of a host cell.

18. The method according to claim 17, wherein said objective protein gene is integrated by homologous recombination.

19. The cell according to claim 11, wherein the concentration of MSX is stepwise increased.

* * * * *